United States Patent
Ye et al.

(10) Patent No.: US 10,898,103 B2
(45) Date of Patent: Jan. 26, 2021

(54) METHODS AND SYSTEMS FOR RECONSTRUCTING MAGNETIC RESONANCE IMAGES

(71) Applicants: SHANGHAI UNITED IMAGING HEALTHCARE CO., LTD., Shanghai (CN); The affiliated Drum Tower hospital of Nanjing university medical school, Jiangsu (CN)

(72) Inventors: Yongquan Ye, Houston, TX (US); Bing Zhang, Jiangsu (CN)

(73) Assignees: SHANGHAI UNITED IMAGING HEALTHCARE CO., LTD., Shanghai (CN); THE AFFILIATED DRUM TOWER HOSPITAL OF NANJING UNIVERSITY MEDICAL SCHOOL, Nanjing (CN)

( * ) Notice: Subject to any disclaimer, the term of this patent is extended or adjusted under 35 U.S.C. 154(b) by 214 days.

(21) Appl. No.: 15/636,773

(22) Filed: Jun. 29, 2017

(65) Prior Publication Data
US 2018/0353098 A1 Dec. 13, 2018

(30) Foreign Application Priority Data
Jun. 7, 2017 (CN) .......................... 2017 1 0422816

(51) Int. Cl.
*A61B 5/055* (2006.01)
*G01R 33/561* (2006.01)
(Continued)

(52) U.S. Cl.
CPC .......... *A61B 5/055* (2013.01); *A61B 5/02042* (2013.01); *A61B 5/489* (2013.01);
(Continued)

(58) Field of Classification Search
None
See application file for complete search history.

(56) References Cited

U.S. PATENT DOCUMENTS 8,588,890 B2   11/2013   Kimura
8,674,691 B2    3/2014   Du
(Continued)

FOREIGN PATENT DOCUMENTS

JP    2011030625 A    2/2011

OTHER PUBLICATIONS

E. MarkHaacke et al., Characterizing Iron Depositopn in Multiple Sclerosis Lesions Using Susceptibility Weighted Imaging, Journal of Magnetic Resonance Imaging, 29: 537-544, 2009.
(Continued)

*Primary Examiner* — Douglas X Rodriguez
(74) *Attorney, Agent, or Firm* — Metis IP LLC

(57) ABSTRACT

The present disclosure relates to a system and method for MRI with respect to vessels and bleedings. The method may include exciting a region of interest by applying an RF pulse, wherein the region of interest includes a vessel region and a bleeding region. The method may further include acquiring a plurality of echo signals related to the region of interest. The method may further include generating one or more magnitude images based on the plurality of echo signals, generating a first image with respect to the vessel region based on the one or more magnitude images, generating one or more phase images based on the plurality of echo signals, and generating a second image with respect to a distribution of susceptibility of the bleeding region based on the one or more phase images.

15 Claims, 9 Drawing Sheets

(51) Int. Cl.
  *G01R 33/48* (2006.01)
  *A61B 5/02* (2006.01)
  *A61B 5/00* (2006.01)
  *G01R 33/24* (2006.01)
  *G01R 33/563* (2006.01)
  *G01R 33/565* (2006.01)
  *G01R 33/50* (2006.01)

(52) U.S. Cl.
  CPC ....... *G01R 33/243* (2013.01); *G01R 33/4818* (2013.01); *G01R 33/5612* (2013.01); *G01R 33/5618* (2013.01); *G01R 33/50* (2013.01); *G01R 33/5616* (2013.01); *G01R 33/5635* (2013.01); *G01R 33/56316* (2013.01); *G01R 33/56545* (2013.01)

(56) References Cited

U.S. PATENT DOCUMENTS

| | | | |
|---|---|---|---|
| 8,886,283 | B1 | 11/2014 | Chen et al. |
| 9,538,936 | B2 | 1/2017 | Kimura et al. |
| 2009/0076374 | A1* | 3/2009 | Kimura .................. A61B 5/055 600/410 |
| 2011/0044524 | A1 | 2/2011 | Wang et al. |
| 2014/0043021 | A1 | 2/2014 | Wang et al. |
| 2015/0084628 | A1 | 3/2015 | Sato et al. |
| 2015/0323635 | A1 | 11/2015 | Haacke |
| 2017/0261584 | A1* | 9/2017 | James ..................... A61B 5/055 |
| 2017/0363699 | A1* | 12/2017 | Ookawa ............. G01R 33/4828 |
| 2018/0231631 | A1 | 8/2018 | Ye et al. |

OTHER PUBLICATIONS

Christian Langkammer et al., Quantitative susceptibility mapping(QSM) as a means to measure brain iron? A post mortem validation study, Neuroimage, 62: 1593-1599, 2012.

Tokunori Kimura et al., Hybrid of Opposite-Contrast MR Angiography (HOP-MRA) Combining Time-of-Flight and Flow-Sensitive Black-Blood Contrasts, Magnetic Resonance in Medicine, 62: 450-458, 2009.

Yongquan Ye et al., Noncontrast-Enhanced Magnetic Resonance Angiography and Venography Imaging with Enhanced Angiograph, Journal of Magnetic Resonance Imaging, 38: 1539-1548, 2013.

Kahryn E. Hammond et al., Development of a robust method for generating 7.0 T multichannel phase images of the brain with application to normal volunteers and patients with neurological diseases, Neuroimage, 39: 1682-1692, 2008.

Wei Feng et al., Catalytic Multiecho Phase Unwrapping Scheme (CAMPUS) in Multiecho Gradient Echo Imaging: Removing Phase Wraps on a Voxel-by-Voxel Basis, Magnetic Resonance in Medicine, 70(1): 117-126, 2013.

Hussein S. Abdul-Rahman et al., Fast and robust three-dimensional best path phase unwrapping algorithm, Applied Optics, 46(26): 6623-6635, 2007.

Ferdinand Schweser et al., Quantitative imaging of intrinsic magnetic tissue properties using MRI signal phase: An approach to in vivo brain iron metabolism, Neuroimage, 54(4): 2789-2807, 2011.

Tian Liu et al., Cerebral Microbleeds : Burden Assessment by Using Quantitative Susceptibility Mapping, Radiology, 262: 269-278, 2012.

Ludovic de Rochefort et al., Quantitative Susceptibility Map Reconstruction from MR Phase Data Using Bayesian Regularization: Validation and Application to Brain Imaging, Magnetic Resonance in Medicine 63:194-206, 2010.

Sam Wharton et al., Susceptibility Mapping in the Human Brain Using Threshold-Based k-Space Division, Magnetic Resonance in Medicine, 63:1292-1304, 2010.

Tian Liu et al., Calculation of Susceptibility Through Multiple Orientation Sampling (COSMOS): A Method for Conditioning the Inverse Problem From Measured Magnetic Field Map to Susceptibility Source Image in ERI, Magnetic Resonance in Medicine 61:196-204, 2009.

Takeshi Funaki et al., Visualization of Periventricular Collaterals in Moyamoya Disease with Flow-sensitive Black-blood Magnetic Resonance Angiography: Preliminary Experience, Neurol Med Chir (Tokyo), 55(3): 204-209, 2015.

Funaki T. et al., Periventricular anastomosis in moyamoya disease: detecting fragile collateral vessels with MR angiography, J Neurosurg, 124(6): 1766-1772, 2016.

Alexander Radbruch et al., Comparison of Susceptibility Weighted Imaging and TOF-Angiography for the Detection of Thrombi in Acute Stroke, PLoS One, 8(5): e63459, 2013.

Muhammad Ayaz et al., Imaging Cerebral Microbleeds Using Susceptibility Weighted Imaging: One Step Toward Detecting Vascular Dementia, J Magn Reson Imaging, 31(1): 142-148, 2010.

Sun H. et al., Quantitative susceptibility mapping using a superposed dipole inversion method: Application to intracranial hemorrhage, Magn Reson Med, 76(3): 761-791, 2016.

The Third Office Action in Chinese Application No. 201710422816.7 dated Nov. 4, 2020, 11 pages.

\* cited by examiner

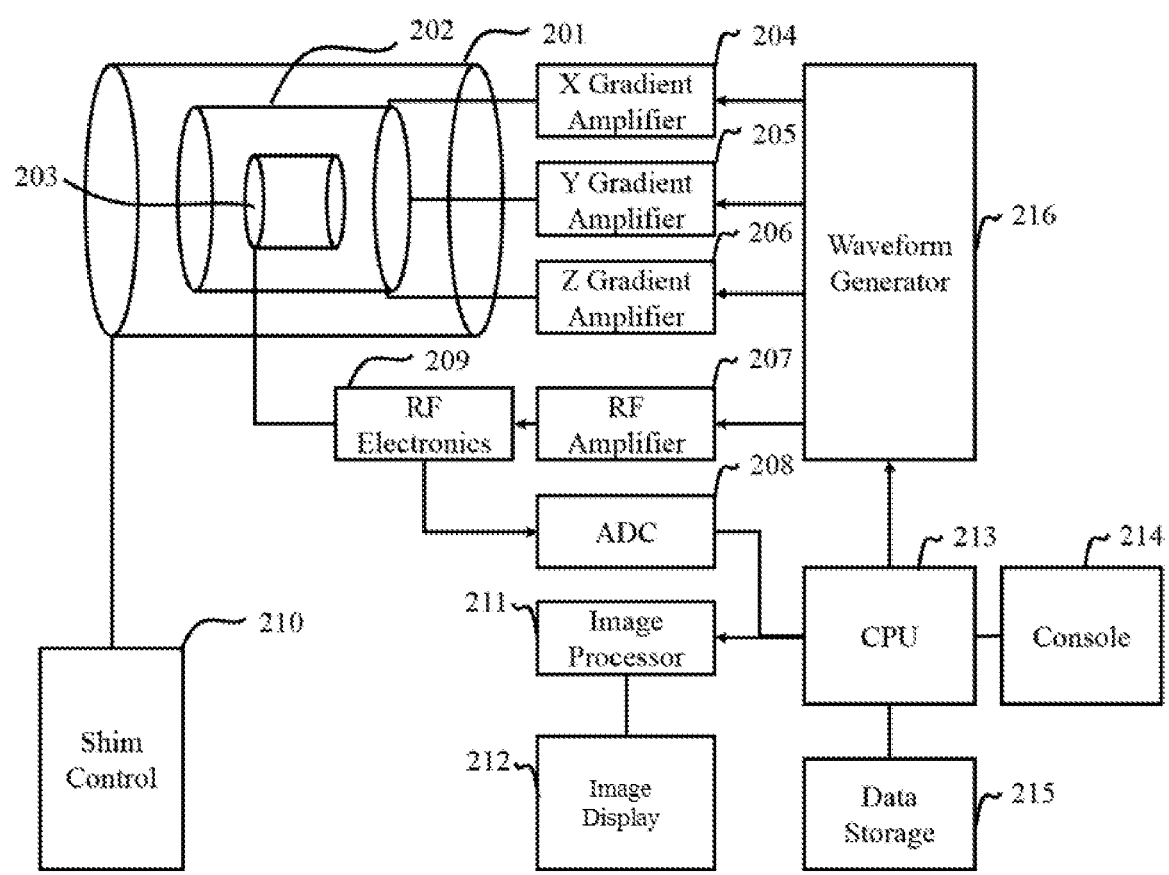
FIG. 2-A

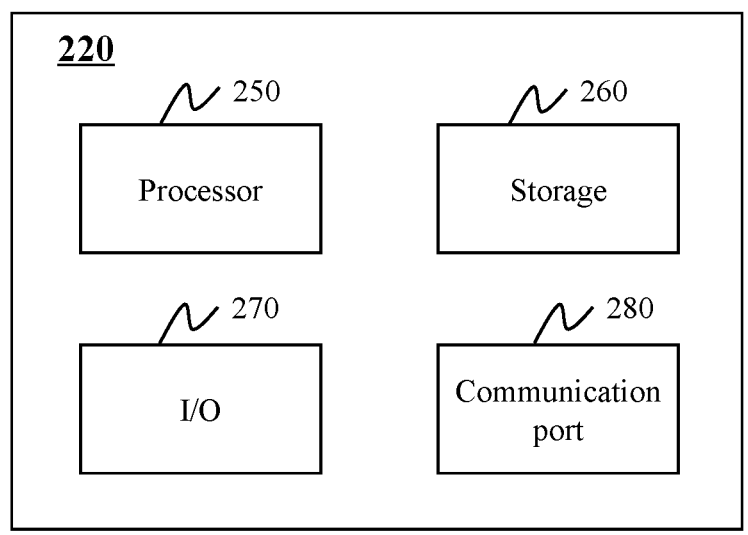
FIG. 2-B

METHODS AND SYSTEMS FOR RECONSTRUCTING MAGNETIC RESONANCE IMAGES

CROSS-REFERENCE TO RELATED APPLICATIONS

The present disclosure claims priority of Chinese Application No. CN 201710422816.7 filed on Jun. 7, 2017, the content of which is hereby incorporated by reference in its entirety.

TECHNICAL FIELD

The present disclosure generally relates to magnetic resonance imaging (MRI), and more particularly, a system and method for MRI with respect to vessels and bleedings.

BACKGROUND

For some vascular diseases, such as Moyamoya, Vascular Malformation, ischemic stroke, the risk of the breakage of vessels is high, which may cause bleeding inside tissues. It is of great importance to determine the spatial relationship between bleedings and vessels around the bleedings for locating the vessel breakage, determining the degree, evaluating the diagnosis and treatment recovery. Therefore, it is desirable to provide high resolution 3D images with highly recognizable imaging contrast for both bleedings and vessels.

SUMMARY

According to an aspect of the present disclosure, a method is provided. The method may be implemented on one machine, including at least one processor and a storage. The method may include exciting a region of interest by applying an RF pulse, the region of interest including a vessel region and a bleeding region. The method may further include acquiring a plurality of echo signals related to the region of interest by applying at least one shot of a multi-echo imaging sequence, the multi-echo imaging sequence may include at least one of one or more flow refocused gradients or one or more flow dephasing gradients, and the plurality of echo signals may be generated by applying the RF pulse. The method may further include generating one or more magnitude images based on the plurality of echo signals, and generating a first image with respect to the vessel region based on the one or more magnitude images. The method may further include generating one or more phase images based on the plurality of echo signals, and generating a second image with respect to a distribution of susceptibility of the bleeding region based on the one or more phase images. The method may further include reconstructing a third image with respect to the region of interest based on the first image and the second image.

In some embodiments, the method may further include determining a spatial relationship between the vessel region and the bleeding region based on the third image.

In some embodiments, the plurality of echo signals may include one or more first echo signals and one or more second echo signals. Generating the one or more magnitude images based on the plurality of echo signals, and generating the first image with respect to the vessel region based on the one or more magnitude images may further include generating a first magnitude image based on at least one of the one or more first echo signals, generating a second magnitude image based on at least one of the one or more second echo signals, and determining the first image with respect to the vessel region based on the first magnitude image or the second magnitude image. The first magnitude image may include a portion corresponding to the vessel region, and the portion corresponding to the vessel region may have lower signal intensities. The second magnitude image may include a portion corresponding to the bleeding region, and the portion corresponding to the bleeding region may have higher signal intensities.

In some embodiments, determining the first image with respect to the vessel region based on the first magnitude image or the second magnitude image may include determining the first image with respect to the vessel region by a linear subtraction between each pixel of the first magnitude image and each pixel of the second magnitude image, or determining the first image with respect to the vessel region by a nonlinear subtraction between each pixel of the first magnitude image and each pixel of the second magnitude image.

In some embodiments, generating the second image with respect to the distribution of susceptibility of the bleeding region may include generating a field distribution map based on the one or more phase images, and determining the second image with respect to the distribution of susceptibility of the bleeding region based on the field distribution map.

In some embodiments, the method may further include performing image rendering on the third image with respect to the region of interest.

According to an aspect of the present disclosure, another method is provided. The method may be implemented on one machine, including at least one processor and a storage. The method may include applying at least one shot of a multi-echo imaging sequence to a region of interest. The region of interest may include a vessel region and a bleeding region. The multi-echo imaging sequence may include one or more RF pulses and one or more gradients. The one or more gradients may include one or more flow refocused gradients or one or more flow dephasing gradients. The one or more gradients may be configured to encode RF signals generated by applying one shot of an RF pulse to the region of interest and to generate a plurality of echo signals. The plurality of echo signals may include a first feature aspect and a second feature aspect. The method may further include generating a first image with respect to the vessel region based on the first feature aspect, and generating a second image with respect to a distribution of susceptibility of the bleeding region based on the second feature aspect. The method may further include reconstructing a third image with respect to the region of interest based on the first image and the second image.

In some embodiments, the first feature aspect may include magnitude information of the plurality of echo signals, and the second feature aspect may include phase information of the plurality of echo signals. Generating the second image with respect to a distribution of susceptibility of the bleeding region based on the second feature aspect may include generating at least one phase image based on the second feature aspect, generating a field distribution map based on the at least one phase image, and determining the second image with respect to the distribution of susceptibility of the bleeding region based on the field distribution map.

In some embodiments, the plurality of echo signals may include a first portion of the plurality of echo signals and a second portion of the plurality of echo signals. The first feature aspect may include magnitude information of the first portion of the plurality of echo signals. The second feature aspect may include magnitude information of the second portion of the plurality of echo signals.

In some embodiments, generating the second image with respect to a distribution of susceptibility of the bleeding region based on the second feature aspect may include generating at least one magnitude image based on the second feature aspect, generating a T2* map based on the at least one magnitude image, and determining the second image with respect to the distribution of susceptibility of the bleeding region based on the T2* map.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 2-A illustrates a system diagram of an exemplary MRI system according to some embodiments of the present disclosure;

FIG. 2-B illustrates exemplary hardware and/or software components of an exemplary computing device on which the processing module may be implemented according to some embodiments of the present disclosure;

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirits and scope of the present disclosure. Thus, the present disclosure is not limited to the embodiments shown, but to be accorded the widest scope consistent with the claims.

It will be understood that the term "system," "module," "unit," and/or "block" used herein are one method to distinguish different components, elements, parts, section or assembly of different level in descending order. However, the terms may be displaced by other expression if they may achieve the same purpose.

It will be understood that when a unit, module or block is referred to as being "on," "connected to" or "coupled to" another unit, module, or block, it may be directly on, connected or coupled to the other unit, module, or block, or intervening unit, module, or block may be present, unless the context clearly indicates otherwise. As used herein, the term "and/or" includes any and all combinations of one or more of the associated listed items.

The terminology used herein is for the purposes of describing particular examples and embodiments only, and is not intended to be limiting. As used herein, the singular forms "a," "an," and "the" may be intended to include the plural forms as well, unless the context clearly indicates otherwise. It will be further understood that the terms "include," and/or "comprise," when used in this disclosure, specify the presence of integers, devices, behaviors, stated features, steps, elements, operations, and/or components, but do not exclude the presence or addition of one or more other integers, devices, behaviors, features, steps, elements, operations, components, and/or groups thereof.

The system and method in the present disclosure is described primarily in regard to providing spatial relationship between vessels and bleedings in a three-dimensional image. The system and the method may generate images with respect to the vessels and the bleeding region, according to echo signals that are generated in response to a same RF pulse. Based on the echo signals generated in response to the same RF pulse, the accuracy of the spatial relationship between the vessels and the bleedings may be significantly improved.

Figure 1:
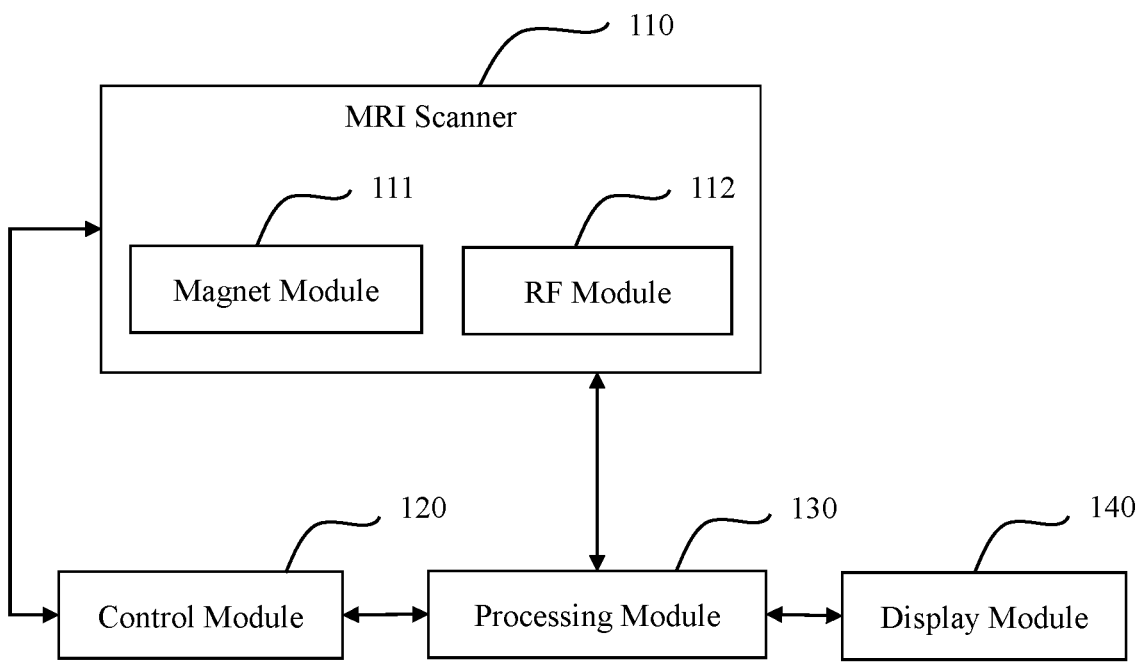
FIG. 1 illustrates an exemplary magnetic resonance imaging (MRI) system according to some embodiments of the present disclosure.

FIG. 1 illustrates an exemplary magnetic resonance imaging system 100 according to some embodiments of the present disclosure. As illustrated, an MRI system 100 may include an MRI scanner 110, a control module 120, a processing module 130, and a display module 140. The MRI scanner 110 may include a magnet module 111 and a radio frequency (RF) module 112. The magnet module 111 may include a main magnetic field generator and/or a gradient magnetic field generator (not shown in FIG. 1). The main magnetic field generator may include a main magnet that creates a static magnetic field $B_0$ during an MRI process. The main magnet may be of various types including, for example, a permanent magnet, a superconducting electromagnet, a resistive electromagnet, etc. The gradient magnetic field generator may generate magnetic field gradients in the X, Y, and/or Z directions. As used herein, the X direction is also referred to as the readout (RO) direction, the Y direction is also referred to the phase encoding (PE) direction, the Z direction is also referred to the slice-select (SS) direction. In the present disclosure, readout direction and frequency encoding direction may be used interchangeably. The gradient magnetic field may encode the spatial information of a subject (to be examined) located in the MRI scanner 110. The RF module 112 may include RF transmitting coils and/or receiving coils. The transmitting coils may transmit RF pulses to excite a region of interest of the subject. Then the region of interest may generate echo signals. The receiving coils may receive the echo signals. In some embodiments, an RF pulse may be an RF pulse with a flip angle of, e.g., 30°, 40°, 60°, etc. In some embodiments, the function, size, type, geometry, position, amount of the magnet module 111 and/or of the RF module 112 may be determined or changed according to one or more specific conditions. For example, according to the difference in function and size, the RF coils may be classified as volume coils and local coils. In some embodiments of the present disclosure, the volume coils may be configured as birdcage coils, transverse electromagnetic coils, saddle coils, Helmholtz coils, etc. In some embodiments of the present disclosure, the local coils may include phased array coils, toroid coil, etc. In some embodiments, the magnet module 111 and the RF module 112 may be designed to surround a subject to form a tunnel type MRI scanner (i.e. a close-bore MRI scanner), or an open MRI scanner (i.e. an open-bore MRI scanner).

The control module 120 may control the magnet module 111 and/or the RF module 112 of the MRI scanner 110, the processing module 130, and/or the display module 140. The control module 120 may receive information from or send information to the MRI scanner 110, the processing module 130, and/or the display module 140. According to some embodiments of the present disclosure, the control module 120 may receive commands from the display module 140 provided by, e.g., a user, and adjust the magnet module 111 and/or RF module 112 to image a region of interest according to the received commands. The processing module 130 may process different kinds of information received from different modules.

For further understanding the present disclosure, several examples are given below, but the examples do not limit the scope of the present disclosure. For example, in some embodiments, the processing module 130 may process MR signals received from the RF module 112 and generate one or more MR images based on the MR signals and deliver the one or more MR images to the display module 140. In some embodiments, the processing module 130 may process data input by a user or an operator via the display module 140, transform the data into specific commands, and supply the commands to the control module 120. The display module 140 may receive input and/or display output information. The input and/or output information may include programs, software, algorithms, data, text, number, images, voice, or the like, or any combination thereof. For example, a user or an operator may input one or more initial parameters or conditions to initiate a scan. In the present disclosure, user and operator may be used interchangeably unless otherwise stated. As another example, some information may be imported from an external resource, such as a floppy disk, a hard disk, a wireless terminal, or the like, or any combination thereof. In some embodiments, the control module 120, the processing module 130, and/or the display module 140 may be integrated into an MRI console. An operator may set parameters in MRI scanning, control the imaging procedure, view the images produced through the MRI console.

It should be noted that the above description of the MRI system 100 is merely provided for the purposes of illustration, and not intended to limit the scope of the present disclosure. For persons having ordinary skills in the art, multiple variations and modifications may be made under the teachings of the present disclosure. For example, the assembly and/or function of the MRI system 100 may be varied or changed according to specific implementation scenarios. Merely by way of example, some other components may be added into the MRI system 100, such as a patient positioning module, a gradient amplifier module, and other devices or modules. Note that the MRI system may be a traditional or a single-modality medical system, or a multi-modality system including, e.g., a positron emission tomography-magnetic resonance imaging (PET-MRI) system, a remote medical MRI system, and others, etc. However, those variations and modifications do not depart from the scope of the present disclosure.

FIG. 2-A illustrates a system diagram 200 of an exemplary MRI system according to some embodiments of the present disclosure. As shown in FIG. 2-A, the main magnet 201 may generate a main magnetic field (B0) to apply to an object (also referred to as subject) exposed inside the field. Gradient coils 202 may be located inside an area defined by the main magnet 201. The gradient coils 202 may generate a second magnetic field or referred to as a gradient field. The gradient coils 202 may include three sets of coils, i.e., X-gradient coils, Y-gradient coils, and/or Z-gradient coils (not shown in FIG. 2-A). In some embodiments, the Z-gradient coils may be designed based on circular (Maxwell) coils, while the X-gradient coils and the Y-gradient coils may be designed on the basis of the saddle (Golay) coil configuration. The three sets of coils may generate three different magnetic fields that are used for position encoding. The gradient coils 202 may allow spatial encoding of MR signals for image construction. The gradient coils 202 may be connected with one or more of an X gradient amplifier 204, a Y gradient amplifier 205, or a Z gradient amplifier 206. One or more of the three amplifiers may be connected to a waveform generator 216. The waveform generator 216 may generate gradient waveforms that are applied to the X gradient amplifier 204, the Y gradient amplifier 205, and/or the Z gradient amplifier 206. An amplifier may amplify a waveform. An amplified waveform may be applied to one of the three sets of coils in the gradient coils 202 to generate a magnetic field in the X-axis, the Y-axis, or the Z-axis, respectively. The gradient coils 202 may be designed for either a close-bore MRI scanner or an open-bore MRI scanner. In some instances, all three sets of coils of the gradient coils 202 may be energized and three gradient fields may be generated thereby. In some embodiments of the present disclosure, the X-gradient coils and Y-gradient coils may be energized to generate the gradient fields in the X direction and the Y direction.

RF coils 203 may generate a third magnetic field that is utilized to generate MR signals for image reconstruction. In some instances, the RF coils 203 may include a transmitting coil and a receiving coil (not shown in FIG. 2-A). In some embodiments, the RF coils 203 may be in connection with RF electronics 209 that may be configured or used as one or more integrated circuits (ICs) functioning as a waveform transmitter and/or a waveform receiver. The RF electronics 209 may be connected with an RF amplifier 207 and an analog-to-digital converter (ADC) 208. The waveform generator 216 may generate a pulse waveform. The pulse waveform may be amplified by the RF amplifier 207 and processed by the RF electronics 209 before it is applied on the RF coils 203 to generate an amplified pulse waveform. In some embodiments of the present disclosure, the waveform generator 216 may generate a series of pulse waveforms periodically or constantly.

The RF pulse may be utilized to generate the third magnetic field. With the application of one or more gradient fields, such as, the gradient field in X direction, one or more MR signals may be generated. For instance, an echo train with multiple echoes may be generated. The echo train length (ETL) may be either fixed or variable. For instance, for a same tissue to be imaged, the ETL may be fixed while for different tissues, the ETL may be different. Furthermore, even for a same tissue, the ETL may be variable. The echo train may be received by the receiving coils of the RF coils 203. Then the echo train may be sent to the RF electronics 209, and transmitted to the ADC 208 for digitization. The echo train may be demodulated and filtered in the RF electronics 209. Subsequently, the echo train may be processed by an image processor 211, e.g., with the assistance of the CPU 213, to generate one or more images. A console 214 may communicate through a link with the CPU 213 and provide an interface to one or more operators to control the production and/or display of images on image display 212. The console 214 may include an input device, a control panel (not shown in FIG. 2-A), etc. The input device may be a keyboard, a touch screen, a mouse, a remote controller, or the like, or any combination thereof.

The CPU 213 may control the production of the waveforms in the waveform generator 216, and the production of images in the image processor 211. The CPU 213 may be a central processing unit (CPU), an application-specific integrated circuit (ASIC), an application-specific instruction-set processor (ASIP), a graphics processing unit (GPU), a physics processing unit (PPU), a microcontroller unit, a digital signal processor (DSP), a field programmable gate array (FPGA), an ARM, or the like, or any combination thereof.

The data storage 215 may store received MR signals. When an MRI scan is completed, the data of a scanned object (e.g., a tissue or a specific part of a body) is acquired. A Fourier transform of the data may be performed by, without limitation to, the CPU 213, the image processor 211, or the like, or any combination thereof. After the Fourier transform is completed, one or more images with respect to the scanned object may be generated. The one or more images respect to the scanned object may be stored in the data storage 215. The one or more images respect to the scanned object may be further conveyed to the image display 212 for display.

In some embodiments, a shim control 210 may be utilized to control the homogeneity of the main magnetic field generated by the main field and shim coils 201.

It should be noted that the above description of the MRI system is merely provided for the purposes of illustration, and not intended to limit the scope of the present disclosure. For persons having ordinary skills in the art, multiple variations and modifications may be made under the teaching of the present invention. However, those variations and modifications do not depart from the scope of the present disclosure.

FIG. 2-B illustrates exemplary hardware and/or software components of an exemplary computing device 200 on which the processing module 130 may be implemented according to some embodiments of the present disclosure. As illustrated in FIG. 2-B, the computing device 200 may include a processor 250, a storage 260, an input/output (I/O) 270, and a communication port 280.

The processor 250 may execute computer instructions (e.g., program code) and perform functions of the processing module 130 in accordance with techniques described herein. The computer instructions may include, for example, routines, programs, objects, components, data structures, procedures, modules, and functions, which perform particular functions described herein. For example, the processor 250 may process image data obtained from the MRI scanner 110, data storage 215, and/or any other component of the MRI system 100 and/or MRI system 200. In some embodiments, the processor 250 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors, thus operations and/or method steps that are performed by one processor as described in the present disclosure may also be jointly or separately performed by the multiple processors. For example, if in the present disclosure, the processor of the computing device 200 executes both step A and step B, it should be understood that step A and step B may also be performed by two or more different processors jointly or separately in the computing device 200 (e.g., a first processor executes step A and a second processor executes step B, or the first and second processors jointly execute steps A and B).

The storage 260 may store data/information obtained from the MRI scanner 110, the processing module 130, data storage 215, and/or any other component of the MRI system 100 and/or MRI system 200. In some embodiments, the storage 260 may include a mass storage, a removable storage, a volatile read-and-write memory, a read-only memory (ROM), or the like, or any combination thereof. For example, the mass storage may include a magnetic disk, an optical disk, a solid-state drives, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 260 may store one or more programs and/or instructions to perform exemplary methods described in the present disclosure. For example, the storage 260 may store a program for the processing module 130 for determining a regularization item.

The I/O 270 may input and/or output signals, data, information, etc. In some embodiments, the I/O 270 may enable a user interaction with the processing module 130. In some embodiments, the I/O 270 may include an input device and an output device. Examples of the input device may include a keyboard, a mouse, a touch screen, a microphone, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touch screen, or the like, or a combination thereof.

The communication port 280 may be connected to a network to facilitate data communications. The communication port 280 may establish connections between the processing module 130 and the MRI scanner 110, the control module 120, and/or display module 140. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee link, a mobile network link (e.g., 3G, 4G, 5G, etc.), or the like, or a combination thereof. In some embodiments, the communication port 280 may be and/or include a standardized communication port, such as RS232, RS485, etc. In some embodiments, the communication port 280 may be a specially designed communication port. For example, the communication port 280 may be designed in accordance with the digital imaging and communications in medicine (DICOM) protocol.

Figure 3:
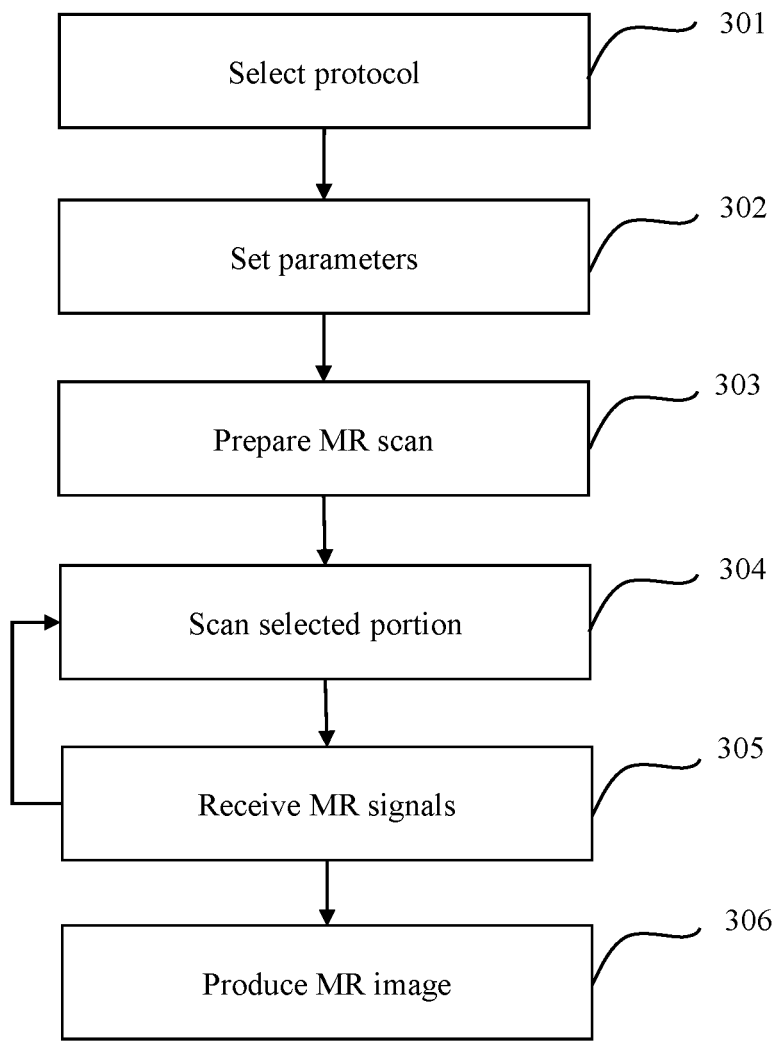
FIG. 3 illustrates an exemplary flowchart of an MRI process according to some embodiments of the present disclosure.

FIG. 3 illustrates an exemplary flowchart of an MRI process using the MRI system according to some embodiments of the present disclosure. In some embodiments, at least a part of process 300 may be performed by or be implemented on one or more components of the MRI system 100.

In 301, one or more protocols may be selected. A protocol may be designed for imaging one or more tissues, diagnosing diseases, and/or configuring clinical scenarios. A protocol may include a certain number of pulse sequences oriented in different planes and/or with different parameters. The pulse sequences may include a spin echo sequence, a gradient echo sequence, a steady state free precession sequence, an inversion recovery sequence, or the like, or any combination thereof. The spin echo sequences may include fast spin echo (FSE), half-Fourier acquisition single-shot turbo spin-echo (HASTE), turbo gradient spin echo (TGSE), or the like, or any combination thereof. When an MR scan is to be conducted, an operator may select a protocol for the scan. For example, for a cranial scan, the operator may select one of the protocols including "Routine Adult Brain," "MR Angiogram Circle of Willis," "Angiographic Enhancement," "Susceptibility Quantification," etc. These protocols described above or other protocols may be stored in the data storage 215 as illustrated in FIG. 2, or other storage devices (e.g., an external storage device or server accessible by the MR system 100).

In 302, one or more parameters may be set. The parameters may be set via the console 214 through a user interface that may be displayed on, e.g., the image display 212 as specified in FIG. 2. The parameters may include image contrast and/or ratio, a region of interest (ROI), slice thickness, an imaging type (e.g., T1 weighted imaging, T2 weighted imaging, proton density weighted imaging, etc.), T1, T2, a spin echo type (spin echo, fast spin echo (FSE), fast recovery FSE, single shot FSE, gradient recalled echo, fast imaging with stead-state procession, and so on), a flip angle value, acquisition time (TA), echo time (TE), repetition time (TR), echo train length (ETL), the number of excitations (NEX), inversion time, bandwidth (e.g., RF receiver bandwidth, RF transmitter bandwidth, etc.), or the like, or any combination thereof.

It should be noted that the above description of the MRI system 100 is merely provided for the purposes of illustration, and not intended to limit the scope of the present disclosure. For persons having ordinary skills in the art, multiple variations and modifications may be made under the teachings of the present disclosure. For example, the number of phases in an echo train may be one, two, three, or more, or equal to the number of echoes. In some embodiments, several echoes may be located in one phase, and the remaining echoes belong to one or more other phases or are not assigned to a phase at all. However, those variations and modifications do not depart from the scope of the present disclosure.

In 303, preparation for the MR scan may be performed. The preparation may include positioning an object, e.g., a selected portion of a subject of interest, within the scanning area, setting the scanning range, tuning and matching shimming coils, adjusting a center frequency, adjusting transmitter attenuation/gain, adjusting signal reception attenuation/gain, setting dummy cycles, or the like, or any combination thereof.

In 304, the selected portion of a subject of interest may be scanned. The scanning may include localizer scans, calibration scans for parallel imaging, automatic pre-scan, or the like, or any combination thereof. For instance, the localizer scans may produce localizer images of low resolution and a large field of view (FOV). Such localizer images may be utilized in subsequent steps. In this step, a pulse sequence including, for example, an RF pulse, may be applied on the selected portion. In some embodiments, the selected portion may include a vessel region and a bleeding region.

MRI is a non-invasive imaging technique that uses a powerful main magnet field to align the nucleus spins in a subject (or a portion thereof). When the subject is exposed in a magnetic field (e.g., the main magnet field $B_0$), the nucleus spins of the subject tend to align with the main magnet field $B_0$, but may still precess at the Larmor frequency. The overall motion of the nucleus spins in the subject, subject to the main magnet field $B_0$, may be denoted as net magnetization (M) that is an averaged value of multiple individual nucleus spins. The net magnetization M may include a longitudinal component (along the Z axis, aligned with the main magnet field $B_0$), and a transverse component (within the XY plane, perpendicular to the main magnet field $B_0$). With the effect of main magnet field $B_0$, M may constitute a longitudinal magnetization vector in the macroscopic view. A second magnetic field oscillating at the Larmor frequency, i.e., RF field $B_1$, may be applied to the net magnetization M to cause the net magnetization M to deviate from the main magnet field $B_0$ direction. During the excitation by an RF field $B_1$, the longitudinal component of the net magnetization M may decrease and the transverse component of the net magnetization M may appear. Merely by way of example, if an RF pulse with a 30° flip angle is applied, when the RF transmitter is turned off, the net magnetization M demonstrates longitudinal component and transverse component. The transverse magnetization may induce a current signal in the RF receiving coils, and the induced current signal may be referred to as an MR signal. Based on one or more gradient fields as described elsewhere in the disclosure, the MR signal may correspond to one or more echo trains including, for example, one or more echo signals, according to the pulse sequence selected in step 301.

In 305, the generated MR signals may be received. Step 305 may be performed by the RF coils 203 as described in FIG. 2. The MR signals may correspond to one or more echo signals, or the like. The one or more echo signals may include one or more feature aspects, for example, a first feature aspect, a second feature aspect. The first feature aspect may refer to magnitude information (e.g., magnitude) of at least one of the plurality of echo signals. The second feature aspect may refer to phase information (e.g., phase) and/or magnitude information (e.g., magnitude) at least one of the plurality of echo signals. It should be noted that step 305 and step 304 may be repeated until sufficient data to generate an image is acquired or an image is generated. One or more operations may be performed on the MR signals to produce images of the selected portion. The operations may further include Fourier transform (FT) of the data, frequency encoding, phase encoding, or the like, or any combination thereof. The operations may include filling data of the MR signals into the Fourier domain (or referred to as the spatial frequency space, or the k-space). For instance, Fourier transform may be a fast Fourier Transform (FFT), a 2-dimentional FT, a 3-dimentional FT, or the like, or any combination thereof. In step 306, one or more images of the selected portion may be produced. The images may be displayed on, e.g., the image display 212 (shown in FIG. 2), or other display devices (e.g., an external display device).

It should be noted that the flowchart described above is provided for the purposes of illustration, not intended to limit the scope of the present disclosure. For persons having ordinary skills in the art, multiple variations and modifications may be reduced to practice in the light of the present disclosure. However, those variations and modifications do not depart from the scope of the present disclosure. For instance, step 301, step 302, and step 303 may be performed sequentially in an order other than that described above in connection with FIG. 3. Alternatively, step 301, step 302, and step 303 may be performed concurrently.

Figure 4:
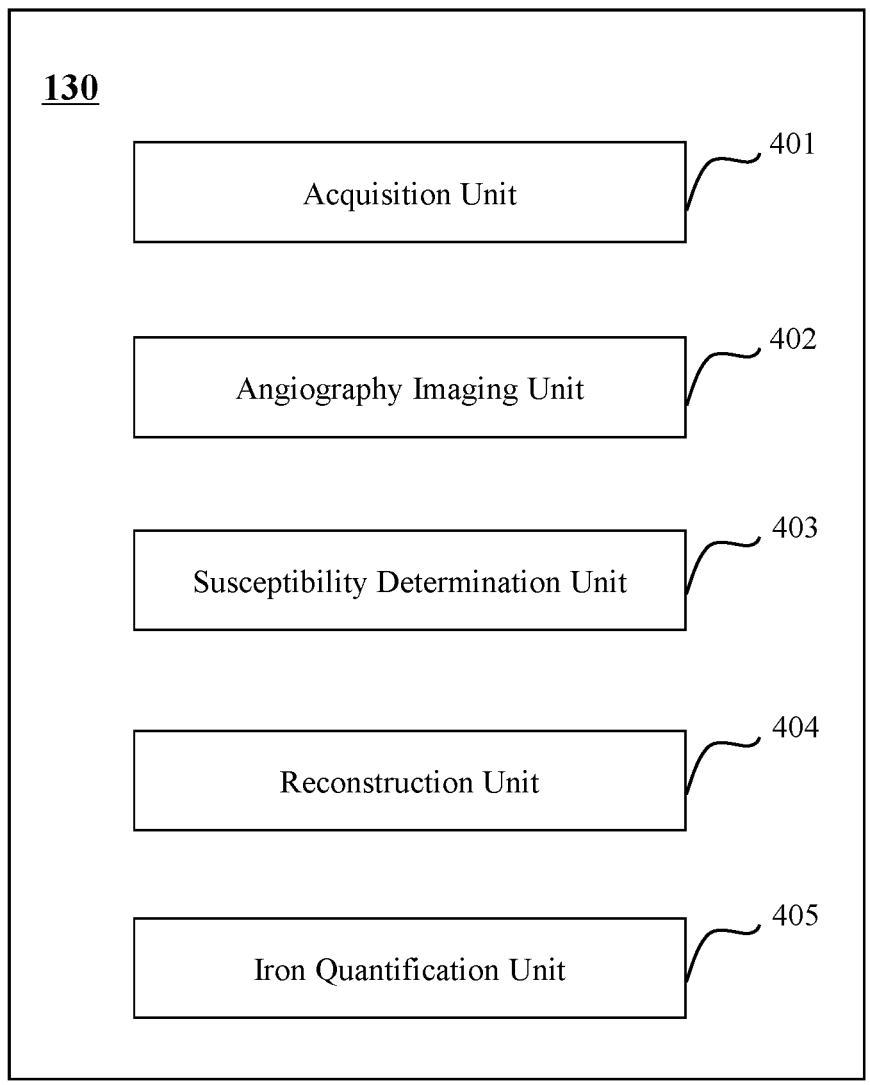
FIG. 4 illustrates a block diagram of an exemplary processing module according to some embodiments of the present disclosure.

FIG. 4 illustrates a block diagram of an exemplary processing module 130 according to some embodiments of the present disclosure. In some embodiments, the processing module 130 may include a processor. The processor may be a central processing unit (CPU), an application-specific integrated circuit (ASIC), an application-specific instruction-set processor (ASIP), a graphics processing unit (GPU), a physics processing unit (PPU), a microcontroller unit, a digital signal processor (DSP), a field programmable gate array (FPGA), an ARM, or the like, or any combination thereof. As illustrated in FIG. 4, the processing module 130 may include an acquisition unit 401, an angiography imaging unit 402, a susceptibility determination unit 403, reconstruction unit 404, and an iron quantification module 405. The units may be connected or otherwise communicate with each other via a wired connection (e.g., a metal cable, an optical cable, a hybrid cable, or the like, or any combination thereof) or a wireless connection (e.g., a Local Area Network (LAN), a Wide Area Network (WAN), a Bluetooth, a ZigBee, a Near Field Communication (NFC), or the like, or any combination thereof).

The acquisition unit 401 may acquire a plurality of echo signals. The plurality of echo signals may be acquired from the MRI scanner 110 (e.g., the receiving coils in the RF module 112) or any storage disclosed elsewhere in the present disclosure. The plurality of echo signals may relate to a region of interest (ROI). In some embodiments, the ROI may include a vessel region, a bleeding region, etc. The vessel region may refer to a region containing one or more blood vessels (arteries and/or veins). The bleeding region may refer to a region containing one or more bleedings. In some embodiments, the plurality of echo signals may be generated using a single-echo sequence or a multi-echo sequence. For example, the plurality of echo signals may be generated using a multi-echo gradient recalled sequence (GRE). More particularly, for example, at least two of the plurality of echo signals may be generated in response to a radio frequency (RF) signal. The plurality of echo signals may be spatially encoded. In some embodiments, the plurality of echo signals may be generated in response to one or more flow refocused gradients, one or more flow dephasing gradients, or a combination thereof. The one or more flow refocused gradients and/or the one or more flow dephasing gradients may be imposed along the slice selection direction (i.e., the Z direction), the phase encoding direction (i.e., the Y direction), and/or the readout direction (i.e., the X direction). In some embodiments, the acquisition unit 401 may include an ADC that converts the echo signals from analog signals to digital signals.

Figure 10:
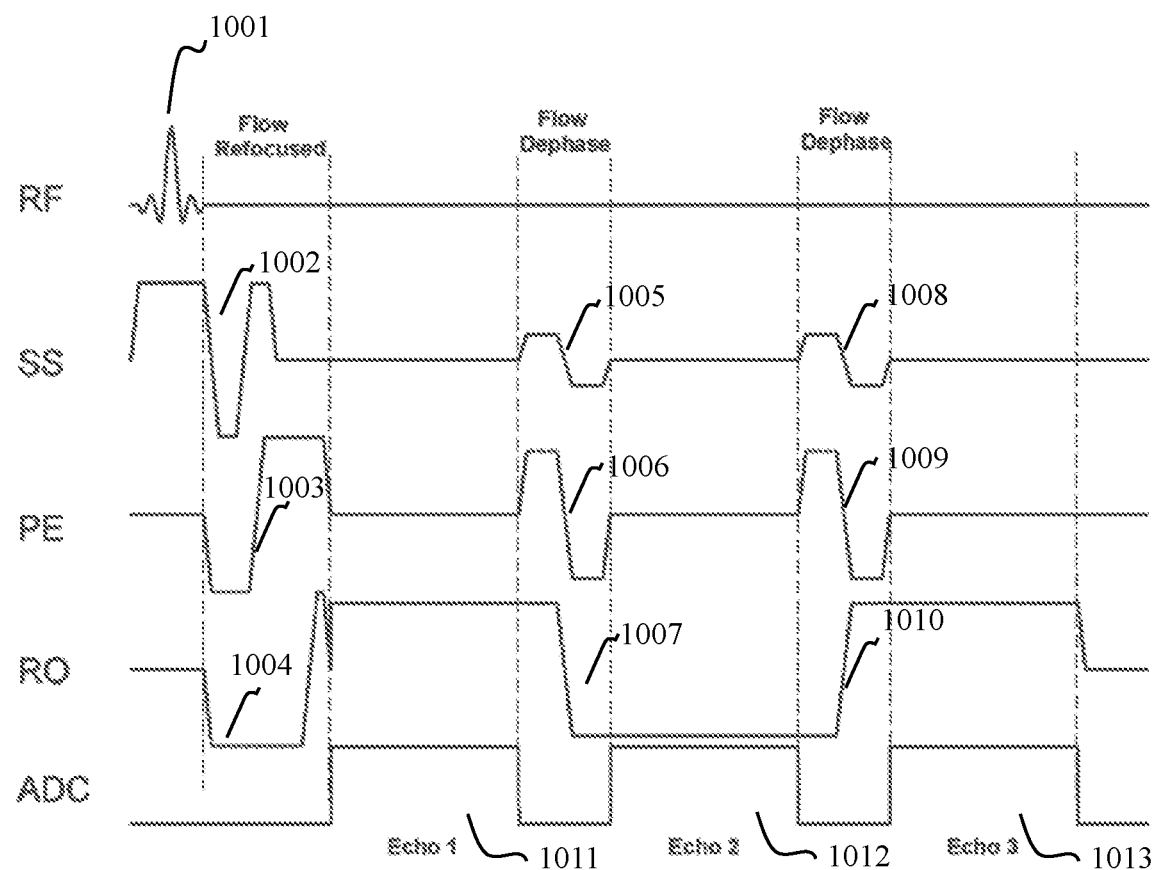
FIG. 10 illustrates an exemplary multi-echo gradient recalled sequence (GRE) including flow refocused gradients and flow dephasing gradients in a single repetition time according to some embodiments of the present disclosure.

The angiography imaging unit 402 may generate an MR image with respect to a vessel region. In some embodiments, the angiography imaging unit 402 may generate the MR image with respect to the vessel region based on at least one of the plurality of echo signals received by the acquisition unit 401. The at least one of the plurality of echo signals may be generated in response to one or more flow refocused gradients, one or more flow dephasing gradients, or a combination thereof. In some embodiments, the angiography imaging unit 402 may generate the MR image with respect to the vessel region based on an enhancement technology. The enhancement technology may enhance the visibility of (e.g., highlight) the vessel region in the MR image. In some embodiments, the enhancement technology may include, for example, providing echo signals for generating an image with positive contrast, and/or negative contrast. The enhancement technology for providing an image with positive contrast may also be referred to as white blood (WB) technique. The enhancement technology for providing an image with negative contrast may also be referred to as black blood (BB) technique. The image with positive contrast may refer to that the vessel region may have higher signal intensities (e.g., brighter) than the background tissue in the image. The image with negative contrast of an image may refer to that the vessel region may have lower signal intensities (e.g., darker) than the background tissue in the image. In some embodiments, the angiography imaging unit 402 may generate a first magnitude image with enhanced positive contrast based on a first echo signal and generate a second magnitude image with enhanced negative contrast based on a second echo signal. As used herein, a magnitude image may refer to an image presenting signal intensity of an echo signal. The portion corresponding to the vessel region in the first magnitude image may have lower signal intensities. The portion corresponding to the vessel region in the second magnitude image may have higher signal intensities. The first echo signal may be generated with an application of a flow refocused gradient. The second echo signal may be generated with an application of a dephasing gradient. An exemplary first echo signal may include echo 1011, and an exemplary second echo signal may include echo 1012 and echo 1013, as shown in FIG. 10. The angiography imaging unit 402 may further determine the MR image with respect to the vessel region based on the first magnitude image and the second magnitude image. The details of determining the MR image with respect to the vessel may be provided in connection with FIGS. 5-7 and the descriptions thereof.

The susceptibility determination unit 403 may generate an MR image with respect to a distribution of susceptibility of a bleeding region. The MR image with respect to a distribution of susceptibility of a bleeding region may refer to an MR image presenting information of susceptibility of the bleeding region. For example, the MR image with respect to a distribution of susceptibility of the bleeding region may include a susceptibility weighted imaging (SWI) image, a Quantitative Susceptibility Mapping (QSM) image, etc. In some embodiments, the susceptibility determination unit 403 may generate the MR image with respect to a distribution of susceptibility of the bleeding region based on at least one of the plurality of echo signals as described elsewhere in the disclosure. In some embodiments, the susceptibility determination unit 403 may generate the MR image with respect to a distribution of susceptibility of a bleeding region based on at least the magnitude information of the plurality of echo signals. For example, the susceptibility determination unit 403 may generate at least one magnitude image based on the magnitude information of the plurality of echo signals. The susceptibility determination unit 403 may generate a T2* map based on the at least one magnitude image. Further, the susceptibility determination unit 403 may generate the MR image with respect to a distribution of susceptibility of a bleeding region based on the T2* map. In some embodiments, the susceptibility determination unit 403 may generate the MR image with respect to a distribution of susceptibility of the bleeding region based on the phase information of the at least one of the plurality of echo signals. The susceptibility determination unit 403 may process the phase information and generate a field distribution map. The field distribution map may refer to an image presenting a field distribution. The susceptibility determination unit 403 may further determine the MR image with respect to a distribution of susceptibility of the bleeding region based on the field distribution map. The details of the MR image with respect to a distribution of susceptibility may be provided in connection with FIGS. 5-9 and the descriptions thereof.

The reconstruction unit 404 may reconstruct an MR image with respect to a vessel region and/or a distribution of susceptibility of a bleeding region. In some embodiments, the reconstruction unit 404 may combine the MR image with respect to a vessel region and the MR image with respect to the distribution of susceptibility of the bleeding region after performing normalization to the MR image with respect to a vessel region and/or the distribution of susceptibility of the bleeding region. For example, the reconstruction unit 404 may add the value of each pixel in the MR image with respect to a vessel region to the value of each corresponding pixel in the MR image with respect to a distribution of susceptibility of the bleeding region. As used herein, the normalization on an image may refer to scaling the values of pixels in the image, such that a feature of the image (e.g., the brightness, the image intensity, etc.) may be changed accordingly. In some embodiments, the reconstruction unit 404 may further perform image rendering on the combined image.

In some embodiments, the processing module 130 may further include an iron) quantification unit 405. The iron quantification unit 405 may determine the iron content in an ROI based on a plurality of echo signals. The iron content may refer to an iron concentration. In some embodiments, the iron concentration may be presented using mass concentration (e.g., μg/g tissue, mg/kg tissue). In some embodiments, the iron quantification unit 405 may determine the iron content based on phase information of the plurality of the echo signals. In some embodiments, the iron content may be determined using phase information of the plurality of the echo signals. Merely by way of example, in a left-handed system, the iron content may be determined according to equations (1), (2), and (3) below:

$$\phi = \gamma^* \Delta B^* TE, \quad (1)$$

$$\Delta B = \Delta \chi^* B_0, \quad (2)$$

$$\Delta \chi \propto c, \quad (3)$$

wherein, $\phi$ denotes the phase information of an image; $\gamma$ denotes the gyromagnetic ratio of iron (Hz/T); TE denotes the echo time of an echo signal corresponding to the image (in second); $\Delta B$ denotes the change in the main magnetic field $B_0$; $\Delta_\chi$ denotes the change in the susceptibility (in ppm); and c denotes the iron concentration.

In some embodiments, the iron content may be determined based on a relationship between a phase unit and the iron content (e.g., the iron concentration). In some embodiments, the iron quantification unit 405 may determine the iron content based on a phase unit. In some embodiments, the phase unit $\phi$ may be determined according to equation (4) below:

$$\phi = 2048^*[(\theta/\pi)+1], \quad (4)$$

wherein, $\phi$ denotes the phase information of an image (e.g., a phase image corresponding to at least one of the plurality of echo signals); and $\phi$ denotes a phase unit.

Descriptions regarding the determination of iron content may be found in, for example, Haacke et al., *Journal of Magnetic Resonance Imaging*, 29: 537-544 (2009), which is hereby incorporated by reference. In some embodiments, the iron quantification unit 405 may determine the iron content in a bleeding region based on the MR image generated via the plurality of echo signals. Descriptions regarding determining the iron content may be found in, for example, Langkammer et al., *Neuroimage*, 62: 1593-1599 (2012), which is hereby incorporated by reference.

It should be noted that the above description of the processing module 130 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, the angiography imaging unit 402 and the susceptibility determination unit 403 may be integrated in an independent module or unit used to process both the magnitude image and the phase information. As another example, the processing module 130 may further include a storage unit (not shown). The storage unit may be used to store the acquired echo signals and/or any intermediate data generated during any process performed by any unit in the processing module 130. As a further example, the units in the processing module 130 may include a storage block respectively, or the units may share a common storage block.

Figure 5:
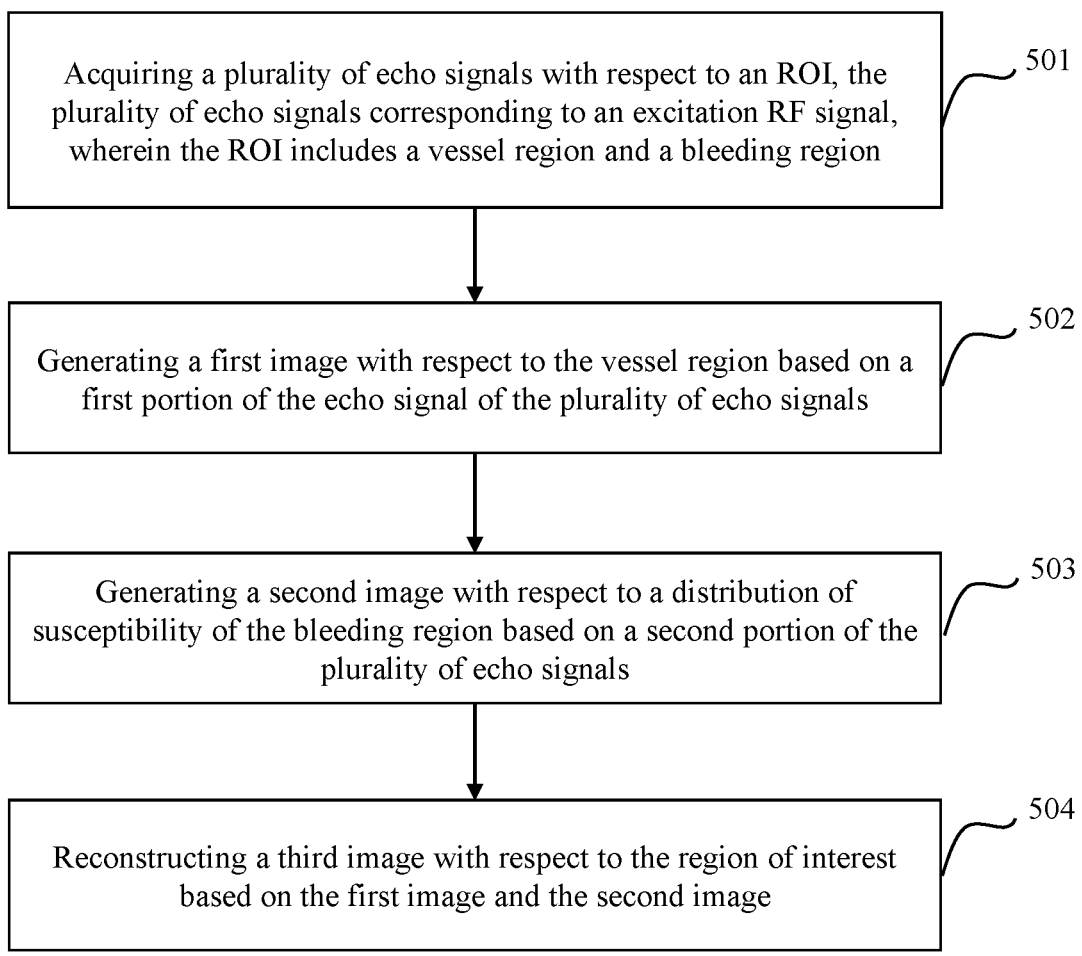
FIG. 5 illustrates an exemplary flowchart for generating an MR image with respect to a vessel region according to some embodiments of the present disclosure.

FIG. 5 illustrates an exemplary flowchart for generating an MR image with respect to a vessel region according to some embodiments of the present disclosure.

In 501, a plurality of echo signals with respect to an ROI may be acquired. The plurality of echo signals may correspond to an RF pulse. The ROI may include a vessel region, a bleeding region, etc. In some embodiments, the acquisition unit 401 may acquire the plurality of echo signals in response to a multi-echo GRE sequence. The plurality of echo signals acquired from the multi-echo GRE sequence may be equidistant or non-equidistant. As used herein, the term "equidistant" may refer to that the interecho spacing ($\Delta$TE) between two adjacent echoes (e.g., echo 1011 and echo 1012 described in FIG. 10) may be equal. The term "non-equidistant" may refer to that the interecho spacing ($\Delta$TE) between two adjacent echoes may be unequal. In some embodiments, the plurality of the echo signals may be generated corresponding to an RF pulse during a repetition time. As used herein, the repetition time may refer to the time between two consecutive RF pulses. The number of the plurality of echo signals corresponding to the RF pulse in a repetition time may be 3, 4, 5, or any suitable positive integer. Merely by way of example, the acquisition unit 401 may acquire 5 echo signals corresponding to an RF pulse in a repetition time at 3 T of the main magnetic field. In some embodiments, the first echo time of the first echo signal may be set to 7 ms. The $\Delta$TE between two adjacent echoes (e.g., the first echo signal and the second echo signal, the second echo signal and the third echo signal, the third echo signal and the forth echo signal, the forth echo signal and the fifth echo signal, etc.) may be set to 5 ms. The plurality of echo signals may be generated in response to a slice selection gradient, a phase encoding gradient, a readout gradient, or a combination thereof. The slice selection gradient, the phase encoding gradient, or the readout gradient may include a flow refocused gradient, a flow dephasing gradient, or a combination thereof. As shown in FIG. 10, the echo signals 1011, 1012 and 1013 are generated after the RF pulse 1001. The echo signal 1011 is generated in response to the flow refocused gradient 1002 in the slice selection direction, the flow refocused gradient 1003 in the phase encoding direction and the flow refocused gradient 1004 in the readout direction. The echo signals 1012 is generated in response to the flow dephasing gradient 1005 in the slice selection direction, the flow dephasing gradient 1006 in the phase encoding gradient and the flow dephasing gradient 1007 in the readout direction.

In 502, a first image with respect to the vessel region may be generated based on a first portion of the plurality of echo signals. In some embodiments, the generation of the first image may be performed by the angiography imaging unit 402. In some embodiments, the first image may refer to an MR image with great contrast (e.g., white blood contrast) of the blood vessels (e.g., the arteries and the veins). In some embodiments, the angiography imaging unit 420 may generate the first image using an enhancement technology. In some embodiments, the enhancement technology may be performed using a contrast agent within the vessel region during the scanning. In some embodiments, the enhancement technology may include, providing echo signals for generating an image with positive contrast, and/or negative contrast. For example, the angiography imaging 420 unit may determine a first magnitude image with positive contrast and a second magnitude image with negative contrast. The angiography imaging 420 unit may further determine the first image based on the first magnitude image and the second magnitude image. In some embodiments, the first portion of the plurality of echo signals may include at least an echo signal generated in response to a flow refocused gradient in the slice selection direction, the readout direction, and/or the phase encoding direction. As another example, the first portion of 1 of the plurality of echo signals may include at least an echo signal generated in response to a flow dephasing gradient in the slice selection direction, the readout direction, and/or the phase encoding direction. Specifically, the first portion of the plurality of echo signals may include an echo signal generated in response to a flow refocused gradient and two echo signals generated in response to two flow dephasing gradients. The details of the generation of the first image with respect to the vessel region may be provided in connection with FIGS. 6-7 and the description thereof.

In 503, a second image with respect to a distribution of susceptibility of the bleeding region may be generated based on a second portion of the plurality of echo signals. In some embodiments, the generation of the second image may be performed by the angiography imaging unit 402. The second image may present information of susceptibility with respect to the bleeding region. In some embodiments, the angiography imaging unit 402 may generate the second image based on magnitude information. The magnitude information may be acquired from the second portion of the plurality of echo signals. Merely by way of example, the angiography imaging unit 402 may generate a T2* map based on the magnitude information. The angiography imaging unit 402 may further generate the second image based on the T2* map. In some embodiments, the angiography imaging unit 402 may generate the second image based on phase information. The phase information may be acquired from the second portion of the plurality of echo signals. In some embodiments, the second image may include an SWI image, a QSM, etc. In some embodiments, the second portion of the plurality of echo signals may include at least an echo signal generated in response to a flow refocused gradient in the slice selection direction, the readout direction, and/or the phase encoding direction. In some embodiments, the second portion of the plurality of echo signals may include at least an echo signal generated in response to a flow dephasing gradient in the slice selection direction, the readout direction, and/or the phase encoding direction. In some embodiments, the second portion of the plurality of echo signals may be the same with or different from the first portion of the plurality of echo signals. The details of the generation of the second image with respect to a distribution of susceptibility of the bleeding region may be provided in connection with FIGS. 8-9, and the description thereof.

In 504, a third image with respect to the region of interest may be reconstructed based on the first image and the second image. In some embodiments, the reconstruction of the third image may be performed by the reconstruction unit 404. In some embodiments, the third image may present a great contrast of the vessel region and the bleeding region. In some embodiments, the reconstruction unit 404 may combine the first image and the second image after performing a normalization to the first image, the second image, or a combination thereof. For illustration purpose, the pixel values of the first image may be in a range from –4095 to 4096, and the pixel values of the second image may be in a range from –1 ppm to 1 pm. The reconstruction unit 404 may adjust the pixel values of the first image and/or the second image, to make the pixel values of the first image and the second image fall in an approximate level. For example, the reconstruction unit 404 may scale down the pixel values of the first image such that that scaled first image may present a similar feature (e.g., the brightness, the image intensity, etc.) with the second image. Then, the reconstruction unit 404 may combine the first image and the second image. The combination may include adding the pixel value of each pixel in the first image to the pixel value of the corresponding pixel in the second image. The corresponding pixel in the second image and the each pixel in the first image may have the same coordinates (e.g., a horizontal coordinate, a vertical coordinate, etc.).

It should be noted that the above description of the process 500 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, one or more steps may be added in the process 500. For example, the iron content in the ROI may be determined by, for example, an iron quantification unit, after the generation of the second image.

In some embodiments, the iron content may be determined based on the second image. For example, the iron content may be determined based on a relationship between the susceptibility of the second image and the icon content. In some embodiments, the relationship may be described as equation (5) below:

$$\chi=0.00097*c-0.040, \qquad (5)$$

wherein, $\chi$ denotes the mean susceptibility value of a tissue that is presented in the second image (e.g., occipital white matter), and c denotes the iron concentration (e.g., mg/kg wet tissue).

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, the generation of the first image and the second image may be performed simultaneously or successively. As another example, a storing step or a caching step may be added between any two steps, in which signals or intermediate data may be stored or cached.

Figure 6:
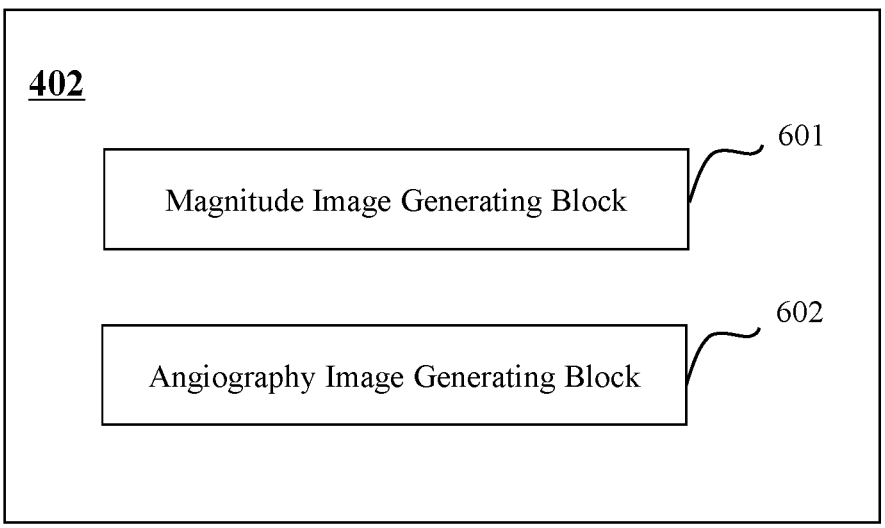
FIG. 6 illustrates a block diagram of an exemplary angiography imaging unit according to some embodiments of the present disclosure.

FIG. 6 illustrates a block diagram of an exemplary angiography imaging unit 402 according to some embodiments of the present disclosure. The angiography imaging unit 402 may include a magnitude image generating block 601 and an angiography image generating block 602.

The magnitude image generating block 601 may generate one or more magnitude images based on a plurality of echo signals. The plurality of echo signals may be acquired from the acquisition unit 401. The one or more magnitude images may include one or more original magnitude images, and/or one or more virtual magnitude images. The original magnitude images may refer to magnitude images generated from the plurality of echo signals. The virtual magnitude images may refer to magnitude images computed based on the plurality of echo signals. In some embodiments, the magnitude image generating block 601 may generate the one or more original magnitude images using single channel imaging, or multi-channel imaging. The multi-channel imaging may include Sum of Square (SOS), Adaptive Coil Combine (ACC), Sensitivity Encoding (SENSE), Simultaneous Acquisition of Spatial Harmonics (SMASH), Generalized Auto-calibrating Partially Parallel Acquisition (GRAPPA), etc. The magnitude image generating block 601 may generate an original magnitude image corresponding to one of the plurality of echo signals. Furthermore, the magnitude image generating block 601 may generate a virtual magnitude image corresponding to an echo time based on the one or more original magnitude images. Descriptions regarding the generation of the virtual magnitude image may be found in, for example, U.S. application Ser. No. 15/314,059 filed on Nov. 25, 2016, which is hereby incorporated by reference.

In some embodiments, the magnitude image generating block 601 may generate one or more first magnitude images with higher magnitude signal (i.e., higher signal intensities), and/or one or more second magnitude images with lower magnitude signal. The one or more first magnitude images may include a vessel region with higher signal intensities (e.g., brighter) than the background tissue. The one or more first magnitude images may be generated based on one or more echo signals generated in response to one or more flow refocused gradients. The one or more second magnitude images may include a vessel region with lower signal intensities (e.g., darker) than the background tissue. The one or more second magnitude images may be generated based on one or more echo signals generated in response to one or more flow dephasing gradients.

The angiography image generating block 602 may generate an angiography image with respect to a vessel region. In some embodiments, the angiography image may include an image with enhanced positive contrast, an image with enhanced negative contrast, or the like, or a combination thereof. For example, the angiography image generating block 602 may determine one of the one or more first magnitude images as the angiography image. As another example, the angiography image generating block 602 may determine one of the one or more second magnitude images, or an average magnitude image of the one or more second magnitude images as the angiography image. The average magnitude image may be acquired by a simple average of the one or more second magnitude images, or a weighted average of the one or more second magnitude images. As still another example, the angiography image generating block 602 may determine the angiography image based on both of the first magnitude image and the second magnitude image. Specifically, the angiography image may be determined by a subtraction between the first magnitude image and the second magnitude image. The subtraction may include a linear subtraction, a nonlinear subtraction, or a combination thereof. The linear subtraction may include a simple weighted subtraction (SWS), a spatial frequency weighted subtraction (FWS). The nonlinear subtraction may include a self-weighted subtraction. Descriptions regarding the linear subtraction (e.g., SWS, FWS, etc.) may be found in, for example, Kimura et al., *Magnetic Resonance in Medicine*, 62: 450-458 (2009), which is hereby incorporated by reference. Descriptions regarding the nonlinear subtraction (e.g., self-weight subtraction) may be found in, for example, Ye et al., *Journal of Magnetic Resonance Imaging*, 38: 1539-1548 (2013), which is hereby incorporated by reference.

It should be noted that the above description of the angiography imaging unit is merely provided for the purposes of illustration, and not intended to limit the scope of the present disclosure. For persons having ordinary skills in the art, multiple variations or modifications may be made under the teachings of the present disclosure. For example, the assembly and/or function of the angiography imaging unit 402 may be varied or changed. In some embodiments, the magnitude image generating block 601 and the angiography image generating block 602 may share one storage block. In some embodiments, the magnitude image generating block 601 and the angiography image generating block 602 may have their own storage blocks, respectively. In some embodiments, the angiography imaging unit 402 may further include a magnitude image processing block. The magnitude image processing block may process the magnitude information of one or more magnitude images. However, those variations and modifications do not depart from the scope of the present disclosure.

Figure 7:
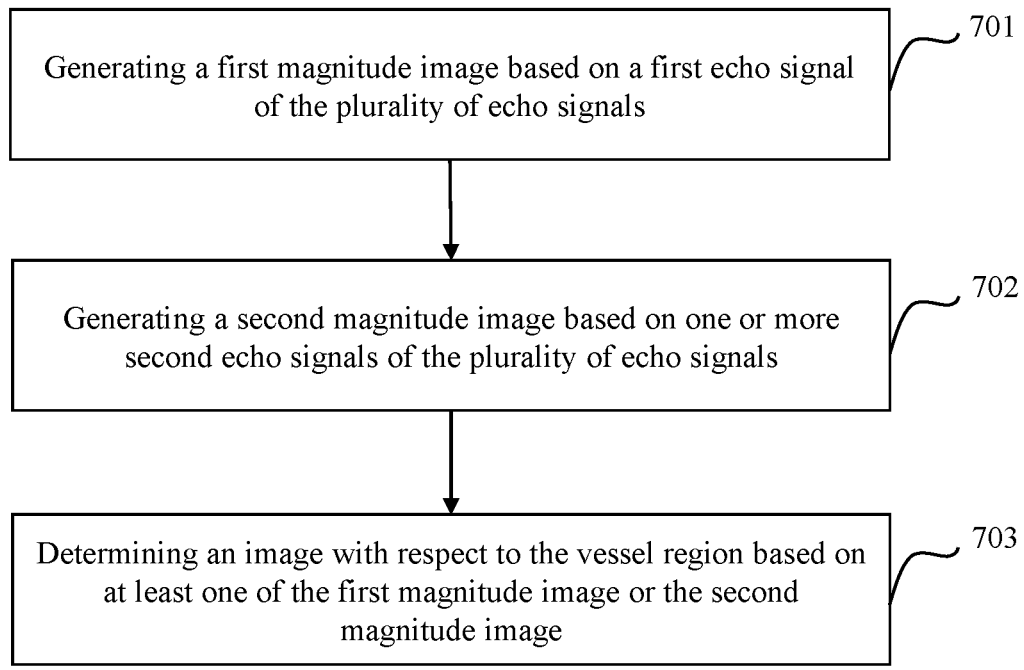
FIG. 7 illustrates an exemplary flowchart for generating a first image with respect to the vessel region according to some embodiments of the present disclosure.

FIG. 7 illustrates an exemplary flowchart for generating an image with respect to the vessel region according to some embodiments of the present disclosure. In some embodiments, the process 700 may be performed in connection with step 502 as described in FIG. 5. The process 700 may be performed by the angiography imaging unit 402.

In 701, a first magnitude image may be generated based on a first echo signal of the plurality of echo signals. The generation of the first magnitude image may be performed by the magnitude image generating block 601. In some embodiments, the magnitude image generating block 601 may generate the first magnitude image using single channel imaging, or multi-channel imaging. In some embodiments, the first echo signal may be generated in response to a flow refocused gradient. Referring to FIG. 10, the first echo signal 1011 is generated in response to the flow refocused gradient 1002, 1003, and 1004 after the excitation of the RF pulse 1001. The echo time (TE) of the first echo signal of the plurality of echo signals may be longer than other echo signal(s) of the plurality of echo signals, for example, 7 ms, 8 ms, 9 ms, etc.

In 702, a second magnitude image may be generated based on one or more second echo signals of the plurality of echo signals. The generation of the second magnitude image may be performed by the magnitude image generating block 601. In some embodiments, the magnitude image generating block 601 may generate the second magnitude images using single channel imaging, or multi-channel imaging. In some embodiments, the one or more second echo signals may be generated in response to one or more flow dephasing gradients. Referring to FIG. 10, one second echo signals, i.e., the echo signal 1012, is generated in response to the flow dephasing gradient 1005, 1006, and 1007 after the excitation of the RF pulse 1001 and the first echo signal 1011. Another second echo signals, i.e., the echo signal 1013, is generated in response to the flow dephasing gradient 1008, 1009, and 1010 after the excitation of the RF pulse 1001, the first echo signal 1011 and the echo signal 1012. The one or more second echo signals of the plurality of echo signals may be equidistant or non-equidistant. For example, the interecho spacing ($\Delta TE$) between two adjacent echoes of the one or more second echo signals may be equal. The $\Delta TE$ may be 5 ms, 6 ms, etc. In some embodiments, more than one magnitude images may be generated based on different second echo signals, e.g., echo signal 1012 and echo signal 1013, respectively. The magnitude image generating block 601 may determine one of the one or more magnitude images as the second magnitude image. Alternatively or additionally, the magnitude image generating block 601 may determine an average magnitude image of the more than one magnitude images as the second magnitude image. The average magnitude image may include a simple average magnitude image, and a weighted average magnitude image, etc., as described elsewhere in the disclosure.

In 703, an image with respect to the vessel region may be determined based on at least one of the first magnitude image or the second magnitude image. In some embodiments, the angiography image generating block 602 may determine the first magnitude image as the image with respect to the vessel region. In some embodiments, the angiography image generating block 602 may determine the second magnitude image as the image with respect to the vessel region. In some embodiments, the angiography image generating block 602 may perform a subtraction between the first magnitude image and the second magnitude image to obtain a resultant image, and determine the resultant image as the image with respect to the vessel region. The subtraction may include a linear subtraction (e.g., SWS, FWS), a nonlinear subtraction (e.g. self-weighted subtraction), or a combination thereof.

For illustration purpose, the SWS may be described as equation (6) below:

$$S_H = S_W - \alpha S_B, \quad (6)$$

wherein, $S_H$ denotes a magnitude signal of a resultant image (e.g., the image with respect to the vessel region determined according to step 703); $S_W$ denotes a magnitude signal of a first magnitude image; $S_B$ denotes a magnitude signal of a second magnitude image; and a denotes a scaling factor. In some embodiments, the value of a may be 0.5, 1.0, 1.5, 2.0, or any suitable numbers.

Similarly, the FWS may be described as equation (7) below:

$$S_H = H_W[S_W] - H_B[S_B], \quad (7)$$

wherein, $H_W$ denotes a spatial filter operator for $S_W$; and $H_B$ denotes a spatial filter operator for $S_B$. The spatial filter operators may be determined based on weighted summation of a standard filter operator and a high pass filter operator.

The self-weighted subtraction may be described as equation (8) below:

$$\Delta S = S^2 - \alpha S'^2, \quad (8)$$

wherein, $\Delta S$ denotes a magnitude signal of a resultant image (e.g., the image with respect to the vessel region determined according to step 703); S denotes a magnitude signal of a first magnitude image; $S_B$ denotes a magnitude signal of a second magnitude image; and a denotes a weighting factor for the subtraction between $S^2$ and $S'^2$. In some embodiments, the value of a may be 0.5, 0.75, 1.0, 1.25, 1.5, or any suitable number.

Descriptions regarding the linear subtraction (e.g., SWS, FWS, etc.) may be found in, for example, Kimura et al., *Magnetic Resonance in Medicine*, 62: 450-458 (2009), which is hereby incorporated by reference. Descriptions regarding the nonlinear subtraction (e.g., self-weight subtraction) may be found in, for example, Ye et al., *Journal of Magnetic Resonance Imaging*, 38: 1539-1548 (2013), which is hereby incorporated by reference.

It should be noted that the above description of the process for the image with respect to the vessel region is merely provided for the purposes of illustration, and not intended to limit the scope of the present disclosure. For persons having ordinary skills in the art, multiple variations or modifications may be made under the teachings of the present disclosure. For example, in some embodiments, the generation of the first magnitude image and the second magnitude image may be performed simultaneously or successively. However, those variations and modifications do not depart from the scope of the present disclosure.

Figure 8:
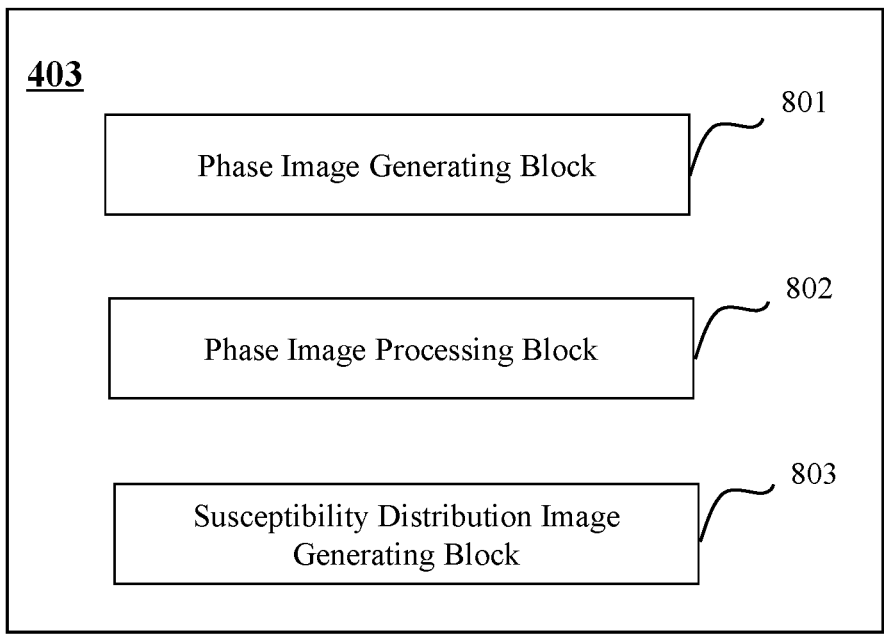
FIG. 8 illustrates a block diagram of an exemplary susceptibility determination unit according to some embodiments of the present disclosure.

FIG. 8 illustrates a block diagram of an exemplary susceptibility determination unit 403 according to some embodiments of the present disclosure. The susceptibility determination unit 403 may include a phase image generating block 801, a phase image processing block 802, and a susceptibility distribution image generating block 803.

The phase image generating block 801 may generate one or more phase images based on a plurality of echo signals acquired from, for example, the acquisition unit 401. In some embodiments, the phase image generating block 801 may generate the one or more original phase images using single channel imaging, or multi-channel imaging. The multi-channel imaging may include the weighted average technique, the adaptive coil combine (ACC) algorithm, the technique of performing zero-order phase correction to the other channels relative to a reference channel and then performing multi-channel combination, etc. Descriptions regarding the weighted average technique may be found in, for example, Hammond et al., *Neuroimage*, 39: 1682-1692 (2008), which is hereby incorporated by reference. In some embodiments, the phase image generating block 801 may generate an original phase image corresponding to one of the plurality of echo signals. The phase image generating block 801 may generate a virtual phase image corresponding to an echo time according to the one or more original phase images. Descriptions regarding the generation of the virtual phase image may be found in, for example, U.S. application Ser. No. 15/314,059 filed on Nov. 25, 2016, which is hereby incorporated by reference.

The phase image processing block 802 may process the phase information of a phase image. The phase image may be generated or acquired from the phase image generating block 801. In some embodiments, the phase image processing block 802 may include a phase unwrapping sub-block (not shown in FIG. 8) and a background field processing sub-block (not shown in FIG. 8). The phase unwrapping sub-block may reduce or remove phase wrap-around artifacts in a phase image. As used herein, a phase wrap may refer to the phase that is wrapped in an interval of $2\pi$ (e.g., $(-\pi,\pi]$). Exemplary techniques used to reduce or remove phase wrap-around artifacts may include the phase unwrapping algorithm based on a single-echo sequence or a multi-echo sequence. Descriptions regarding the algorithm based on a multi-echo sequence may be found in, for example, Feng et al., *Magnetic Resonance in Medicine*, 70(1): 117-126 (2013), which is hereby incorporated by reference. Descriptions regarding the algorithm based on a single-echo sequence may be found in, for example, Abdul-Rahman et al., *Applied Optics*, 46(26): 6623-6635 (2007), which is hereby incorporated by reference. In some embodiments, the phase unwrapping algorithm based on a single-echo sequence may include a global error-minimization algorithm (e.g., the least-square algorithm, etc.), a residue-balancing algorithm, a quality-guided algorithm, or the like, or a combination thereof. The background field processing sub-block may reduce or remove the effect of the background field in the phase image. The background field may be caused by the inhomogeneity of the main magnetic field $B_0$. Exemplary techniques used to remove the background field may include Sophisticated Harmonic Artifact Reduction for Phase data (SHARP). Descriptions regarding SHARP may be found in, for example, Schweser et al., *Neuroimage*, 54(4): 2789-2807 (2011), which is hereby incorporated by reference.

In some embodiments, the phase image processing block 802 may generate a processed phase image with the phase wrap-around artifact removed or reduced, and/or with the background field removed or reduced.

The susceptibility distribution image generating block 803 may generate an image with respect to the distribution of susceptibility of a bleeding region (also referred to as "susceptibility image") based on a phase image or a processed phase image. The susceptibility image may refer to an image presenting information of susceptibility of the bleeding region. For example, the susceptibility image may include a SWI image, a QSM image, etc. In some embodiments, the susceptibility distribution image generating block 803 may generate a field distribution map based on the phase image or the processed phase image. Then, the susceptibility distribution image generating block 803 may further generate the susceptibility image based on the field distribution map. The generation of the susceptibility image based on the field distribution map may include an ill-posed inverse process. For example, the susceptibility distribution image generating block 803 may conduct a susceptibility inversion. The susceptibility inversion may refer to determining a susceptibility value based on the field distribution map. The technique of susceptibility inversion may include Morphology Enabled Dipole Inversion (MEDI), Bayesian Regularization (BR), Threshold-based k-space Division (TKD), Calculation of Susceptibility through Multiple Orientation Sampling (COSMOS), etc. The MEDI may refer to a technique that exploits the structural consistency between the susceptibility map and the magnitude image reconstructed from the same GRE sequence, and use magnitude information as a priori probability. Descriptions regarding the MEDI may be found in, for example, Liu et al., *Radiology*, 262: 269-278 (2012), which is hereby incorporated by reference. The BR may refer to a technique introducing a priori probability for the likelihood estimation of the inverse process. The priori probability may be determined using Bayesian statistics. Descriptions regarding the BR may be found in, for example, de Rochefort et al., *Magnetic Resonance in Medicine* 63:194-206 (2010), which is hereby incorporated by reference. The TKD may refer to a technique based on the division of the three-dimensional Fourier transforms of high-pass-filtered field distribution maps by a simple function that is the Fourier transform of the convolution kernel linking field and susceptibility, and uses k-space masking to avoid noise enhancement in regions where this function is small. Descriptions regarding the TKD may be found in, for example, Wharton et al., *Magnetic Resonance in Medicine* 63:1292-1304 (2010), which is hereby incorporated by reference. The COSMOS may refer to a technique to stabilize the inverse problem by sampling from multiple orientations. The COSMOS may determine noise effects using a weighted least-squares technique. Descriptions regarding the COSMOS may be found in, for example, Liu et al., *Magnetic Resonance in Medicine* 61:196-204 (2009), which is hereby incorporated by reference.

It should be noted that the above description of the susceptibility determination unit is merely provided for the purposes of illustration, and not intended to limit the scope of the present disclosure. For persons having ordinary skills in the art, multiple variations or modifications may be made under the teachings of the present disclosure. For example, the assembly and/or function of the susceptibility determination unit 403 may be varied or changed. In some embodiments, the phase image generating block 801, the phase image processing block 802, and the susceptibility distribution image generating block 803 may share one storage block. In some embodiments, the phase image generating block 801, the phase image processing block 802, and the susceptibility distribution image generating block 803 may have their own storage blocks, respectively. However, those variations and modifications do not depart from the scope of the present disclosure.

Figure 9:
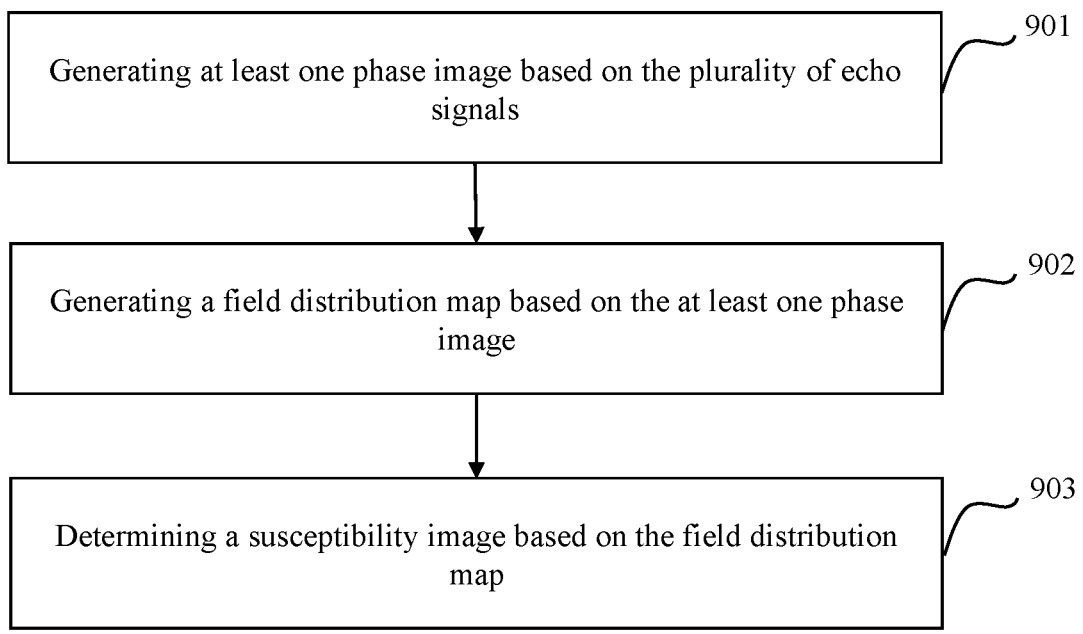
FIG. 9 illustrates an exemplary flowchart for generating a second image with respect to the distribution of susceptibility of the bleeding region according to some embodiments of the present disclosure.

FIG. 9 illustrates an exemplary flowchart for generating a susceptibility image according to some embodiments of the present disclosure.

In 901, at least one phase image may be generated based on the plurality of echo signals. The generation of the at least one phase image may be performed by the phase image generating block 801. As described elsewhere in the disclosure, the plurality of echo signals may include echo signals generated in response to one or more flow refocused gradients and/or one or more flow dephasing gradients. The phase image may include a plurality of pixels, each of which has a phase information. In some embodiments, the phase information at a pixel location of the at least one phase image may be represented according to equation (9) below:

$$\varphi(r,t)=\gamma B_{Local}(r)t+\gamma B_{BG}(r)t+\varphi_0(r)+\varepsilon(r,t), \quad (9)$$

wherein, $\varphi(r, t)$ denotes the phase information, r denotes the pixel location, t denotes the echo time of the echo signal responsible for generating the at least one phase image, $\gamma$ denotes the gyromagnetic ratio of the proton, $B_{Local}(r)$ denotes the local field distribution, $B_{BG}(r)$ denotes the background field distribution, $\varphi_0(r)$ denotes a constant phase offset, and $\varepsilon(r, t)$ denotes the noise-induced phase variation.

In 902, a field distribution map may be generated based on the at least one phase image. The generation of the field distribution map may be performed by the susceptibility distribution image generating block 803. The field distribution map may refer to a presentation of the field distribution in an image, including the local field distribution. In some embodiments, the at least one phase image may be processed as described elsewhere in the disclosure, and the field distribution map may be generated based on the processed phase image. For illustration purpose, a relationship between the phase information at a pixel location of the phase image or the processed phase image and the field distribution may be expressed as equation (10) below:

$$\varphi_p(r,t)=\gamma B_{Local}(r)t, \quad (10)$$

wherein, $\varphi_p(r, t)$ denotes the phase information at a pixel location corresponding to an echo time without the effect of the interference factors (e.g., a phase wrap-around artifact and/or a background field, etc.), r denotes the pixel location, t denotes the echo time, $\gamma$ denotes the gyromagnetic ratio of the proton, and $B_{Local}(r)$ denotes the local field distribution.

In some embodiments, the field distribution map may be generated by fitting equation (10). As used herein, fitting (also referred to as "curve fitting") refers to the process of constructing a curve, or a mathematical function, that has a best fit to a number of data points, possibly subject to one or more constraints. In some embodiments, the fitting result may be associated with the number of the data points (e.g., phase images corresponding to different echo times). In some embodiments, the number of data points needed for fitting may range from 2 to 20, which means that 2-20 echo signals corresponding to different echo times may be used for fitting. In some embodiments, the technique of generating the filed distribution map may include linear regression, extrapolation, a graphing method, or the like, or any combination thereof.

In 903, a susceptibility image may be determined based on the field distribution map. Step 903 may be performed by the susceptibility distribution image generating block 803. The susceptibility image may refer to an image presenting information of susceptibility of the bleeding region. For example, the susceptibility image may include a SWI image, a QSM image. In some embodiments, the susceptibility image may be generated by a susceptibility inversion as described elsewhere in the disclosure, e.g., the susceptibility distribution image generating block 803 and the description thereof.

FIG. 10 illustrates an exemplary multi-echo GRE sequence 1000 including flow refocused gradients and flow dephasing gradients during a single repetition time according to some embodiments of the present disclosure. The repetition time may refer to the time between the applications of two consecutive RF pulses. The GRE sequence shown in FIG. 10 may be applicable for application in the MRI system described elsewhere in the present disclosure.

As illustrated in FIG. 10, the GRE sequence 1000 includes an RF pulse 1001. The RF pulse 1001 may be used to tip a portion of the longitudinal magnetization of an ROI into the transverse plane. Three echo signals including an echo signal 1011, an echo signal 1012, and an echo signal 1013 are acquired from the GRE sequence sequentially during the repetition time. The three echo signals may be further converted from analog signals to digital signals by an ADC.

The flow refocused gradients, including a gradient 1002, a gradient 1003, and a gradient 1004, are applied along the slice selection direction, the phase encoding direction, and the readout direction, respectively. The first flow dephasing gradients, including a gradient 1005, a gradient 1006, and a gradient 1007, are applied along the slice selection direction, the phase encoding direction, and the readout direction, respectively. The second flow dephasing gradients, including a gradient 1008, a gradient 1009, and a gradient 1010, are applied along the slice selection direction, the phase encoding direction, and the readout direction, respectively. The polarities of the first dephasing gradient 1005 and the second dephasing gradient 1008 imposed before two adjacent echoes (the echo 1012 and the echo 1013) along the slice selection direction are the same. The polarities of the first dephasing gradient 1006 and the second dephasing gradient 1009 imposed before two adjacent echoes (the echo 1012 and the echo 1013) along the phasing encoding direction are the same. The polarities of the first dephasing gradient 1007 and the second dephasing gradient 1010 imposed before two adjacent echoes (the echo 1012 and the echo 1013) along the readout direction are opposite.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "block," "module," "engine," "unit," "component," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C #, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution—e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities of ingredients, properties such as molecular weight, reaction conditions, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

We claim:

1. A method implemented on a computing device having at least one processor and a storage, for magnetic resonance imaging, the method comprising:
acquiring a plurality of echo signals by applying at least a multi-echo imaging sequence to a region of interest, the region of interest including a vessel region and a bleeding region;
generating a first image with respect to the vessel region based on the plurality of echo signals;
generating a second image with respect to a distribution of susceptibility of the bleeding region based on the plurality of echo signals, the second image presenting information of susceptibility of the bleeding region; and reconstructing a third image with respect to the region of interest based on the first image and the second image, the third image presenting a contrast of the vessel region and the bleeding region;

wherein the plurality of echo signals include at least a first echo signal and two second echo signals, wherein generating the first image with respect to the vessel region further comprises:

generating a first magnitude image with respect to the vessel region based on the first echo signal, wherein the vessel region is brighter than a background region in the first magnitude image;

generating a second magnitude image with respect to the vessel region based on the two second echo signals, wherein the vessel region is darker than a background region in the second magnitude image; and determining the first image with respect to the vessel region based on at least one of the first magnitude image and the second magnitude image;

the first echo signal is generated by applying flow refocused gradients after excitation of an RF pulse;

the two second echo signals are generated by applying first flow dephasing gradients and second flow dephasing gradients, respectively, the first flow dephasing gradients including a first dephasing gradient in a slice selection direction, a first dephasing gradient in a phase encoding direction and a first dephasing gradient in a readout direction, the second flow dephasing gradients including a second dephasing gradient in the slice selection direction, a second dephasing gradient in the phase encoding direction and a second dephasing gradient in the readout direction, and polarities of the first dephasing gradient and the second dephasing gradient in the slice selection direction are same, polarities of the first dephasing gradient and the second dephasing gradient in the phase encoding direction are same, polarities of the first dephasing gradient and the second dephasing gradient in the readout direction are opposite.

2. The method of claim 1, wherein acquiring the plurality of echo signals further comprises:

applying one or more flow refocused gradients and one or more flow dephasing gradients along at least one of the slice select direction, the readout direction, or the phase encoding direction.

3. The method of claim 2, wherein the plurality of echo signals are generated in response to the one or more flow refocused gradients or the one or more flow dephasing gradients.

4. The method of claim 1, further comprising:

determining a spatial relationship between the vessel region and the bleeding region based on the third image.

5. The method of claim 1, wherein determining the first image with respect to the vessel region based on the first magnitude image and the second magnitude image comprises:

determining the first image with respect to the vessel region by a linear subtraction or a nonlinear subtraction between the first magnitude image and the second magnitude image.

6. The method of claim 1, wherein generating the second image with respect to the distribution of susceptibility of the bleeding region comprises:

generating at least a phase image based on the plurality of echo signals;

generating a field distribution map based on the at least one phase image; and generating the second image with respect to the distribution of susceptibility of the bleeding region based on the field distribution map.

7. The method of claim 1, wherein generating the second image with respect to the distribution of susceptibility of the bleeding region comprises:

generating at least two magnitude images based on a portion of the plurality of echo signals;

generating a $T2^*$ map based on the at least two magnitude images; and generating the second image with respect to the distribution of susceptibility of the bleeding region based on the $T2^*$ map.

8. The method of claim 1, further comprising:

performing image rendering on the third image with respect to the region of interest.

9. The method of claim 1, wherein reconstructing the third image with respect to the region of interest further comprises:

applying a normalization to at least one of the first image with respect to the vessel region or the second image with respect to the distribution of susceptibility of the bleeding region.

10. The method of claim 1, wherein the plurality of echo signals related to the region of interest includes a first feature aspect and a second feature aspect, wherein the first image with respect to the vessel region is generated based on the first feature aspect, wherein the second image with respect to the distribution of susceptibility of the bleeding region is generated based on the second feature aspect.

11. The method of claim 10, wherein the plurality of echo signals includes a first portion of the plurality of echo signals and a second portion of the plurality of echo signals, wherein the first feature aspect includes magnitude information of the first portion of the plurality of echo signals, and wherein the second feature aspect includes phase information of the second portion of the plurality of echo signals.

12. A method for magnetic resonance imaging, comprising:

applying at least one shot of a multi-echo imaging sequence to a region of interest related to a vessel region and a bleeding region thereof;

scanning the region of interest by using a flow refocused or flow dephasing interleaved multi-echo gradient echo (GRE) sequence;

acquiring a plurality of echo signals related to the region of interest;

determining one or more magnitude images based on at least one of the plurality of echo signals, and generating a first image with respect to the vessel region based on the one or more magnitude images;

determining one or more phase images based on at least one of the plurality of echo signals, and generating a second image based on the one or more phase images, the second image presenting information of susceptibility of the bleeding region; and generating a third image based on the first image and the second image, the third image presenting a contrast of the vessel region and the bleeding region;

wherein the plurality of echo signals include at least a first echo signal and two second echo signals, wherein generating the first image with respect to the vessel region further comprises:

generating a first magnitude image with respect to the vessel region based on the first echo signal, wherein the vessel region is brighter than a background region in the first magnitude image;

generating a second magnitude image with respect to the vessel region based on the two second echo signals, wherein the vessel region is darker than a background region in the second magnitude image; and determining the first image with respect to the vessel region based on at least one of the first magnitude image and the second magnitude image;

the first echo signal is generated by applying flow refocused gradients after excitation of an RF pulse;

the two second echo signals are generated by applying first flow dephasing gradients and second flow dephasing gradients, respectively, the first flow dephasing gradients including a first dephasing gradient in a slice selection direction, a first dephasing gradient in a phase encoding direction and a first dephasing gradient in a readout direction, the second flow dephasing gradients including a second dephasing gradient in the slice selection direction, a second dephasing gradient in the phase encoding direction and a second dephasing gradient in the readout direction, and polarities of the first dephasing gradient and the second dephasing gradient in the slice selection direction are same, polarities of the first dephasing gradient and the second dephasing gradient in the phase encoding direction are same, polarities of the first dephasing gradient and the second dephasing gradient in the readout direction are opposite.

13. A system, comprising:
at least one storage medium storing a set of instructions;
at least one processor in communication with the at least one storage medium, wherein when executing the set of instructions, the at least one processor is configured to cause the system to:
acquire a plurality of echo signals by applying at least one shot of a multi-echo imaging sequence to a region of interest, the region of interest including a vessel region and a bleeding region;
generate a first image with respect to the vessel region based on the plurality of echo signals;
generate a second image with respect to a distribution of susceptibility of the bleeding region based on the plurality of echo signals, the second image presenting information of susceptibility of the bleeding region; and
reconstruct a third image with respect to the region of interest based on the first image and the second image, the third image presenting a contrast of the vessel region and the bleeding region;

wherein the plurality of echo signals include at least a first echo signal and two second echo signals, wherein generate the first image with respect to the vessel region further comprises:

generate a first magnitude image with respect to the vessel region based on the first echo signal, wherein the vessel region is brighter than a background region in the first magnitude image;

generate a second magnitude image with respect to the vessel region based on the two second echo signals, wherein the vessel region is darker than a background region in the second magnitude image; and determine the first image with respect to the vessel region based on at least one of the first magnitude image and the second magnitude image;

the first echo signal is generated by applying flow refocused gradients after excitation of an RF pulse;

the two second echo signals are generated by applying first flow dephasing gradients and second flow dephasing gradients, respectively, the first flow dephasing gradients including a first dephasing gradient in a slice selection direction, a first dephasing gradient in a phase encoding direction and a first dephasing gradient in a readout direction, the second flow dephasing gradients including a second dephasing gradient in the slice selection direction, a second dephasing gradient in the phase encoding direction and a second dephasing gradient in the readout direction, and polarities of the first dephasing gradient and the second dephasing gradient in the slice selection direction are same, polarities of the first dephasing gradient and the second dephasing gradient in the phase encoding direction are same, polarities of the first dephasing gradient and the second dephasing gradient in the readout direction are opposite.

14. The system of claim 13, wherein the at least one processor is further configured to cause the system to:
determine a spatial relationship between the vessel region and the bleeding region based on the third image.

15. The system of claim 13, wherein to generate the second image with respect to the distribution of susceptibility of the bleeding region, the at least one processor is further configured to cause the system to:
generate at least a phase image based on the plurality of echo signals;
generate a field distribution map based on the at least one phase image; and
generate the second image with respect to the distribution of susceptibility of the bleeding region based on the field distribution map.

* * * * *